(12) United States Patent
Baxter, Jr.

(10) Patent No.: US 11,174,206 B2
(45) Date of Patent: Nov. 16, 2021

(54) PROCESSES FOR THE MANUFACTURE OF ISOBUTYLENE, POLYISOBUTYLENE, AND DERIVATIVES THEREOF

(71) Applicant: NTP Tec, LLC, Boerne, TX (US)

(72) Inventor: Clyde Edward Baxter, Jr., League City, TX (US)

(73) Assignee: NTP TEC, LLC, Boerne, TX (US)

( * ) Notice: Subject to any disclaimer, the term of this patent is extended or adjusted under 35 U.S.C. 154(b) by 248 days.

(21) Appl. No.: 16/457,190

(22) Filed: Jun. 28, 2019

(65) Prior Publication Data

US 2020/0002246 A1  Jan. 2, 2020

Related U.S. Application Data

(60) Provisional application No. 62/763,982, filed on Jul. 13, 2018, provisional application No. 62/763,714, filed on Jun. 29, 2018.

(51) Int. Cl.
  *C07C 4/06* (2006.01)
  *C07C 2/08* (2006.01)
  (Continued)

(52) U.S. Cl.
  CPC ............... *C07C 4/06* (2013.01); *B01D 3/143* (2013.01); *B01J 4/001* (2013.01); *B01J 19/0046* (2013.01);
  (Continued)

(58) Field of Classification Search
  CPC .... C07C 4/06; C07C 2/08; C07C 7/04; C07C 5/2506; C07C 4/04; B01J 4/00; B01J 19/0046; B01J 2204/002; B01D 3/143
  See application file for complete search history.

(56) References Cited

U.S. PATENT DOCUMENTS

| 1,885,060 A | 10/1932 | Hoffmann et al. |
| 2,404,788 A | 7/1946 | Burk et al. |

(Continued)

FOREIGN PATENT DOCUMENTS

| WO | 9402243 A1 | 2/1994 |
| WO | 9526818 A1 | 10/1995 |
| WO | 2000013792 A1 | 3/2000 |

OTHER PUBLICATIONS

International Search Report and Written Opinion for Application No. PCT/US2019/039869 dated Sep. 9, 2019.

(Continued)

*Primary Examiner* — Thuan D Dang
(74) *Attorney, Agent, or Firm* — Patterson + Sheridan, LLP

(57) ABSTRACT

In an embodiment, a process to convert a feed includes introducing a feed to an oligomerization catalyst in an oligomerization reactor to form a first reactor effluent; introducing the first reactor effluent to a distillation unit to form a first distillation effluent and a second distillation effluent, the second distillation effluent comprising an oligomer of isobutylene; and introducing the second distillation effluent to a cracking reactor to form a cracking reactor effluent comprising a high purity isobutylene. In another embodiment, an apparatus includes a feed line coupled to a first end of an oligomerization reactor; a first distillation unit coupled with a second end of the oligomerization reactor; a first end of a cracking reactor coupled to a second end of the first distillation unit via a first line; a first end of an isomerization reactor coupled to: a third end of the first distillation unit and the feed line.

20 Claims, 4 Drawing Sheets

(51) Int. Cl.
    *C07C 7/04*         (2006.01)
    *C08F 110/10*    (2006.01)
    *B01J 4/00*         (2006.01)
    *B01J 19/00*       (2006.01)
    *B01D 3/14*        (2006.01)
    *C07C 5/25*        (2006.01)

(52) U.S. Cl.
    CPC .............. *C07C 2/08* (2013.01); *C07C 5/2506* (2013.01); *C07C 7/04* (2013.01); *C08F 110/10* (2013.01); *B01J 2204/002* (2013.01)

(56) References Cited

U.S. PATENT DOCUMENTS

| | | | |
|---|---|---|---|
| 2,484,384 A | 10/1949 | Levine et al. | |
| 2,552,692 A | 5/1951 | Schulze et al. | |
| 2,677,002 A | 4/1954 | Yahnke et al. | |
| 2,721,889 A | 10/1955 | O'Young et al. | |
| 2,766,312 A | 10/1956 | Semiuk et al. | |
| 2,804,411 A | 8/1957 | Anderson et al. | |
| 2,957,930 A | 10/1960 | Jackson et al. | |
| 2,976,338 A | 3/1961 | Thomas | |
| 3,068,301 A | 12/1962 | Hervert et al. | |
| 3,114,785 A | 12/1963 | Hervert et al. | |
| 3,119,884 A | 1/1964 | Allen et al. | |
| 3,131,320 A | 4/1964 | Shinada et al. | |
| 4,152,499 A | 5/1979 | Boerzel et al. | |
| 4,256,913 A | 3/1981 | Jung et al. | |
| 4,306,105 A | 12/1981 | Abernathy et al. | |
| 4,400,565 A | 8/1983 | Darden et al. | |
| 4,407,731 A | 10/1983 | Imai | |
| 4,427,797 A | 1/1984 | Smith | |
| 4,427,941 A | 1/1984 | Riedesel, Jr. et al. | |
| 4,429,177 A | 1/1984 | Morganson et al. | |
| 4,533,651 A | 8/1985 | Masters et al. | |
| 4,558,168 A | 12/1985 | Gussow et al. | |
| 4,605,808 A | 8/1986 | Samson | |
| 4,707,731 A | 11/1987 | Ghazey | |
| 4,915,255 A | 4/1990 | Curtis | |
| 4,935,577 A | 6/1990 | Huss, Jr. et al. | |
| 5,068,487 A | 11/1991 | Theriot | |
| 5,068,490 A | 11/1991 | Eaton | |
| 5,191,044 A | 3/1993 | Rath et al. | |
| 5,268,520 A | 12/1993 | Karn et al. | |
| 5,286,823 A | 2/1994 | Rath | |
| 5,300,701 A | 4/1994 | Cherpeck | |
| 5,326,920 A | 7/1994 | Ho et al. | |
| 5,326,923 A | 7/1994 | Cooper et al. | |
| 5,408,018 A | 4/1995 | Rath | |
| 5,408,108 A | 4/1995 | Nakamura et al. | |
| 5,510,560 A | 4/1996 | O'Young et al. | |
| 5,646,332 A | 7/1997 | Cusumano et al. | |
| 5,663,470 A | 9/1997 | Chen et al. | |
| 5,710,225 A | 1/1998 | Johnson et al. | |
| 5,770,539 A | 6/1998 | Chen et al. | |
| 5,789,335 A | 8/1998 | Chen et al. | |
| 5,910,550 A | 6/1999 | Rath | |
| 5,945,575 A | 8/1999 | Sigwart et al. | |
| 5,962,604 A | 10/1999 | Rath | |
| 6,294,578 B1 | 9/2001 | Arimoto et al. | |
| 6,384,054 B1 | 5/2002 | Woosley et al. | |
| 6,433,238 B1 | 8/2002 | Di Girolamo et al. | |
| 6,441,110 B1 | 8/2002 | Sigwart et al. | |
| 6,525,149 B1 | 2/2003 | Baxter, Jr. et al. | |
| 6,562,013 B1 | 5/2003 | Marasco, Jr. | |
| 6,683,138 B2 | 1/2004 | Baxter, Jr. et al. | |
| 6,710,140 B2 | 3/2004 | Wettling et al. | |
| 6,867,267 B2 | 3/2005 | Lewtas et al. | |
| 6,884,858 B2 | 4/2005 | Baxter, Jr. et al. | |
| 6,952,152 B2 | 10/2005 | Miya et al. | |
| 7,411,104 B2 | 8/2008 | Yun et al. | |
| 7,498,396 B2 | 3/2009 | Baxter, Jr. et al. | |
| 8,791,216 B2 | 7/2014 | Baxter, Jr. | |
| 8,816,028 B2 | 8/2014 | Baxter, Jr. | |
| 9,040,645 B2 | 5/2015 | Baxter, Jr. | |
| 9,637,422 B2 | 5/2017 | Kim et al. | |
| 2012/0238716 A1 | 9/2012 | Baxter, Jr. | |
| 2018/0018808 A1 | 1/2018 | Punjani et al. | |

OTHER PUBLICATIONS

Wilson, Karen et al., "Synthesis of a Supported Solid Acid BF3 Catalyst", J. of Chem. Soc., Chem. Commun., 1998, pp. 2135-2136.

International Search Report and Written Opinion for Application No. PCT/2018/018808.

Indian Examination Report dated Mar. 29, 2021 for Application No. 202147003975.

PROCESSES FOR THE MANUFACTURE OF ISOBUTYLENE, POLYISOBUTYLENE, AND DERIVATIVES THEREOF

CROSS-REFERENCE TO RELATED APPLICATIONS

This application claims benefit of U.S. Provisional Patent Application Ser. No. 62/763,714, filed Jun. 29, 2018, the entirety of which is herein incorporated by reference, and to U.S. Provisional Patent Application Ser. No. 62/763,982, filed Jul. 13, 2018, the entirety of which is herein incorporated by reference.

FIELD

The present disclosure relates to processing of C4 streams. The present disclosure also relates to apparatus for processing of C4 streams.

BACKGROUND

Olefin plants have historically cracked heavier feedstocks, including naphtha and gas oils, to produce ethylene and propylene. Byproducts of the cracking operations include crude C4 streams (CC4) that can contain butadiene, isobutylene, 1-butene, and 2-butenes (cis and trans isomers). These CC4 streams are sent to an off-site processing facility mainly to extract and recover the butadiene fraction, highly valuable to the rubber industry. The stream after butadiene extraction is known as raffinate-1. Raffinate-1 has historically been used as a feedstock for high purity isobutylene production. To produce high purity isobutylene, the isobutylene in the raffinate-1 stream is typically removed by reacting it with methanol to make methyl tert-butyl ether ("MTBE"), and the MTBE can be back-cracked to produce high purity isobutylene. One of the drawbacks to this method of producing high purity isobutylene is the alcohol impurities and waste. The stream after removing isobutylene is known as raffinate-2 and contains 1-butene and 2-butenes. 1-Butene and 2-butenes are known as normal butylenes. Because normal butylenes have little economic value, refiners may not send the raffinate-2 streams to off-site processors, and/or may flare the normal butylenes.

Currently, olefin plants are shifting their operations to crack lighter feedstocks, such as ethane, to produce ethylene and propylene. CC4 streams also occur as a byproduct of this cracking, with the CC4 streams containing mostly 1-butene and 2-butenes, with very low amounts of butadiene (as low as less than 2%) and isobutylene. The ethylene and propylene are valuable to the plastics industry, but since the CC4 streams contain such small amounts of butadiene and isobutylene, the CC4 streams have very little value.

Therefore, there is a need for an improved process to convert the 1-butene and 2-butenes in a feedstock (e.g., a CC4 stream, raffinate-1, or raffinate-2) to a product containing high purity isobutylene and minimal amounts of the 1-butene and 2-butenes, and such conversion can take place on site at the olefin plant. Further, there is a need for an improved process to convert 1-butene and 2-butenes in a feedstock to a product containing high reactive polyisobutylene.

SUMMARY

In an embodiment, a process to convert a feed is provided which includes introducing a feed comprising isobutylene to an oligomerization catalyst in an oligomerization reactor to form a first reactor effluent comprising one or more oligomers of isobutylene; introducing the first reactor effluent to a first distillation unit to form a first distillation effluent and a second distillation effluent, the second distillation effluent comprising one or more oligomers of isobutylene; and introducing the second distillation effluent to a cracking reactor to form a cracking reactor effluent, the cracking reactor effluent comprising a high purity isobutylene.

In another embodiment, a process to convert a feed is provided which includes introducing a feed comprising isobutylene to an oligomerization catalyst in an oligomerization reactor to form a first reactor effluent comprising one or more oligomers of isobutylene; introducing the first reactor effluent to a first distillation unit to form a first distillation effluent and a second distillation effluent, the second distillation effluent comprising one or more oligomers of isobutylene; introducing the second distillation effluent to a cracking reactor to form a cracking reactor effluent, the cracking reactor effluent comprising a high purity isobutylene; introducing the first distillation effluent to an isomerization reactor to form an isomerized product effluent, the isomerized product effluent enriched in isobutylene; combining the isomerized product effluent with the feed comprising isobutylene; and introducing the isomerized product effluent to the oligomerization reactor.

In another embodiment, an apparatus is provided which includes a feed line coupled to a first end of an oligomerization reactor; a first distillation unit coupled with a second end of the oligomerization reactor; a first end of a cracking reactor coupled to a second end of the first distillation unit via a first line; an isomerization reactor coupled to: a third end of the first distillation unit at a first end of the isomerization reactor; and the feed line.

BRIEF DESCRIPTION OF THE FIGURES

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, for the disclosure may admit to other equally effective embodiments.

DETAILED DESCRIPTION

Figure 1:
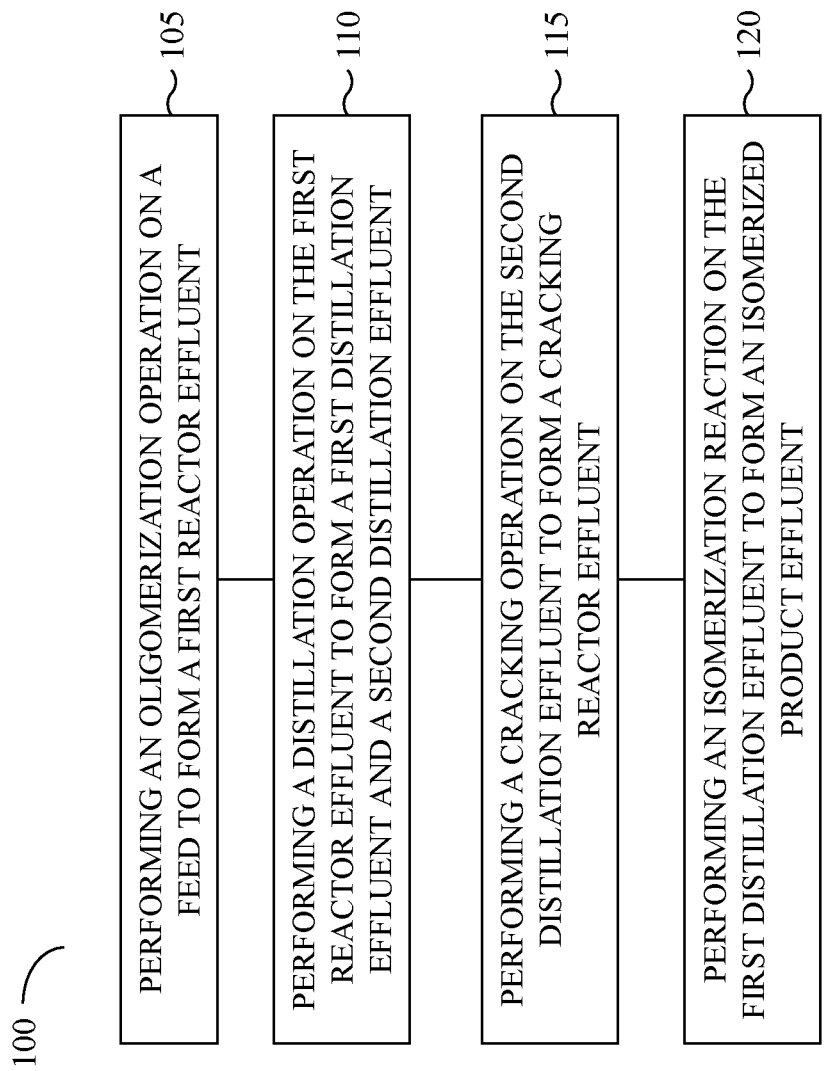
FIG. 1 is a flow diagram of a method of processing C4 according to some embodiments.

The present disclosure provides a novel processing scheme to convert the normal butylenes (e.g., 1-butene and 2-butenes) in crude C4 streams to a product containing isobutylene and minimal amounts of the normal butylenes. Such a process can provide for an economically efficient production of isobutylene. Moreover, the present disclosure includes using that isobutylene formed to make polyisobutylene ("PIB") and high reactive polyisobutylene ("HR-PIB"). Furthermore, the present disclosure includes processes for the conversion of crude C4 streams at the olefin plant instead of sending the crude C4 streams to an off-site processing facility.

Advantageously, the conversion processes disclosed herein can provide a valuable use for the low-value normal butylenes, such as for the production of isobutylene. Instead of flaring the normal butylenes and/or sending the streams containing normal butylenes to off-site processors, the conversion processes disclosed herein advantageously can be performed on-site.

In addition, the present disclosure advantageously provides a process that can convert all, or nearly all, of the isobutylene to PIB, e.g., HR-PIB. The present disclosure provides that the conversion of isobutylene to PIB can be integrated with the C4 conversion process to isobutylene such that all or nearly all of the butylenes (e.g., normal butylenes and isobutylene) in a feedstock are converted to PIB.

For the purposes of this present disclosure and the claims thereto, and unless otherwise specified, "stream," "feed," and "feedstock" may be used interchangeably.

For purposes of this present disclosure and the claims thereto, and unless otherwise specified, "normal butylenes" includes 1-butene and 2-butenes (e.g., cis-2-butene and trans-2-butene).

Part of the present disclosure relates to the manufacture of low molecular weight (Mn) PIB in the range of from about 350 daltons to about 10,000 daltons. High molecular weight PIB is typically in the range of from about 50,000 daltons to about 10,000,000 daltons. About 70% of the low molecular weight PIB manufactured is used as a reactive intermediate in the production of fuel and lubricant additives. The remainder is used in the production of caulks, sealants and other industrial applications in which the physical properties of the PIB, such as viscosity, water barrier properties, and tackiness, are the basis of the applications.

Typically, low molecular weight PIB is made by polymerizing butylenes, particularly isobutylene, contained in industrial butylene streams produced as byproducts in olefin plants. Olefin plants steam crack various hydrocarbon streams including naphtha, gas oils, and more recently lighter hydrocarbons to produce ethylene and propylene. The CC4 streams from these plants contain butadiene in addition to normal butylenes, isobutylene, and butanes. Historically, these streams have been collected and processed in separate C4 processing facilities to extract the butadiene for use in rubber production. The resulting substantially butadiene free streams are referred to as raffinate-1 and contain the residual normal butylenes, isobutylene, and butanes. These raffinate-1 streams have historically been the feedstock for PIB production.

Conventionally, PIB production is generally carried out in continuous stirred tank reactors (CSTR) normally operating at sub-ambient temperatures using $AlCl_3$ catalysis with reaction times in the range of 30-60 minutes. Mn is controlled by reaction temperature with high Mn made at lower temperatures and lower Mn made at higher reaction temperatures. Typically, the reaction temperature can be in the range of 20° F. to 80° F. Many of these processes are commonly referred to as Cosden processes, such as that disclosed in U.S. Pat. No. 2,957,930, which is incorporated by reference herein in its entirety.

Since other butylenes, in addition to isobutylene, are contained in the feed streams, the PIB produced can contain significant amounts, typically up to 25%, of normal butylene moieties in the polymer chain. Technically, these polymers are not polyisobutylene but are more correctly polybutylenes (PB).

Cosden processes using raffinate-1 streams as feedstocks give very low yields of PIB based on the total stream amount. This is because raffinate-1 streams can contain 20% or lower isobutylene with the balance being normal butylenes and butanes. Normal butylenes have lower reactivity in the polymerization reactions compared to isobutylene, and the butanes do not react. Therefore, yields of PIB based on the total amount of raffinate-1 may be 50% or lower. Even isobutylene extraction techniques—such as methyl tert-butyl ether back cracking—to give pure isobutylene for the feed, only yields the isobutylene that was already contained in the raffinate-1 stream. The normal butylenes are not utilized.

PIB contains one double bond per molecule located somewhere in the polymer chain, typically towards the end of the chain. In applications where the polybutylene is used as a reactive intermediate, such as in the manufacture of fuel and lubricant additives, PIB has low reactivity. Until relatively recently, the low reactivity was enhanced by various techniques, such as by chlorination of the PIB prior the derivatization reactions. Although somewhat effective, this technique requires removal of the chlorine residues post-reaction.

In the late 1970's to early 1980's a new type of PIB was introduced, made from isobutylene streams containing essentially no normal butylenes, using special catalysis and operating procedures, in which a very large proportion of the double bond locations are at the terminal position and next to the terminal position in the polymer chain. These double bond configurations are known as alpha vinylidene and beta vinylidene olefin isomers respectively, with the alpha vinylidene configuration preferred. These true polyisobutylenes are referred to as high reactive polyisobutylenes (HR-PIB) because the reactivity in the derivative reactions, particularly to make fuel and lubricant additives, is greatly enhanced, especially in the case of alpha vinylidene and thus requires no chlorination. True HR-PIB is polyisobutylene in which the alpha vinylidene content is greater than 75% and typically greater than 80%. Various operational aspects and catalysts compositions for the manufacture of HR-PIB may be found in U.S. Pat. Nos. 5,962,604; 5,326,920; 5,300,701; 5,068,490, which are incorporated by reference herein in their entirety.

Typically, these early HR-PIB processes use liquid $BF_3$ complex catalysts to catalyze the polymerization of PIB. The complexes are made from $BF_3$ and various alcohols, ethers, or combinations thereof. The complexes can be unstable and can breakdown into non-reactive species at normal operating temperatures and pressures and are made in situ from $BF_3$ gas and the corresponding alcohol and/or ether on-site at the polymerization facility. $BF_3$ gas is highly toxic and represents a substantial risk to operational personnel and thus requires a significant capital investment to meet all safety and environmental requirements. $BF_3$ methanol complexes as the polymerization catalysts have also been developed. These complexes can be more stable and can be made off-site at a $BF_3$ manufacturing facility. Various operational aspects and catalyst compositions may be found in U.S. Pat. No. 7,498,396, which is incorporated by reference herein in its entirety.

Liquid catalysts, such as liquid $BF_3$ complex catalysts, however, must typically be quenched post reaction by water washing. Water washing is very difficult, requiring many additional downstream operations, including a series of large mixer/settler units generating copious amounts of waste water containing fluorides that must be disposed. Liquid catalyst removal, therefore, is a significant bottleneck and represents a substantial capital and operational expense. Conventional HR-PIB processes also need long residence times to effect the polymerization reaction. Residence times, also referred to as reaction times, in these HR-PIB processes are on the order of 30-60 minutes and longer. This means that, for a given capacity, relatively large and extensive reactor units can be required with a corresponding increase in capital costs.

Typical HR-PIB production plants use isobutylene feeds that do not contain normal butylenes, or use raffinate-1 type feeds. However, as discussed above, the yields of HR-PIB based on the amount of raffinate feed is low. Typical methods to improve the yield of HR-PIB from raffinate streams include integration of a high purity isobutylene generating unit in the HR-PIB plant. This high purity isobutylene generating unit can extract isobutylene from crude C4 streams by selectively reacting the contained isobutylene with an alcohol to produce a tert-butyl ether, which is then separated from the non-reactive butylenes and butanes and cracked back to a relatively pure isobutylene with regeneration of the alcohol. The back cracking of methyl tert-butyl ether (MTBE) is an example of such a process. Another typical method discloses extracting isobutylene from CC4 and raffinate streams by back cracking tert-butyl glycol di-ethers to substantially pure isobutylene. See U.S. Pat. No. 9,637,422. The use of glycol, like the MTBE process, remains inefficient. In yet another typical method, the 1-butene in a CC4 or raffinate stream is isomerized to 2-butene and the isobutylene then separated from the higher boiling 2-butene by distillation. In each case, only the isobutylene contained in the CC4 streams is reacted. The normal butylenes do not react and are not utilized. Some of these CC4 streams contain very low levels of isobutylene with normal butylenes as the major contained olefin. Therefore, large amounts of normal butylenes are not utilized.

In some embodiments, the present disclosure includes a processing scheme such that all or nearly all of the butylenes, e.g., normal butylenes and isobutylene, in a CC4 stream can be converted to substantially pure isobutylene. The production of the substantially pure isobutylene can then be integrated with an HR-PIB unit for the production of HR-PIB. In at least one embodiment, the conversion of the butylenes to substantially pure isobutylene can be about 100%. In at least one embodiment, the conversion of isobutylene to HR-PIB can be about 100% with a selectivity to HR-PIB of about 100%.

In some embodiments, the production of HR-PIB can utilize a solid dispersible catalyst and/or fast reactor technology (e.g., a tubular loop reactor). Advantageously, the processes described herein are more cost-efficient than conventional processes.

In some embodiments, the processes described herein can be retrofitted to existing PIB plants that use Cosden processes. Further, these existing PIB plants, can also be retrofitted to use solid dispersible $BF_3$ complex catalysts employing fast-reactor technology with all of the attended benefits and with the further benefit of converting the Cosden PIB product to a HR-PIB.

Existing HR-PIB plants using raffinate streams and other crude streams can also be retrofitted to use the processes described herein. Further, these HR-PIB plants can also be retrofitted with fast-reactor technology where not currently used.

Owing to the lower value of CC4 and raffinate streams isobutylene produced from these streams by the novel scheme disclosed herein advantageously provides a very cost effective source of isobutylene, especially when integrated with a PIB unit or an HR-PIB unit.

The unit operations to produce isobutylene, as described herein, can include an isobutylene oligomerization unit in which the isobutylene in the CC4 feed is selectively oligomerized to dimers and higher oligomers, and an oligomer cracking unit in which the isobutylene dimers and oligomers are cracked to substantially pure isobutylene. The unreacted normal butylenes from the oligomerization operation can be passed through an isomerization process unit (such as a skeletal isomerization process, SKIP, unit) in which the normal butylenes are isomerized to a mixture in which the amount of isobutylene is maximized. This isobutylene enriched effluent form the isomerization process unit can then be cycled back to the incoming CC4 feed completing the overall process loop. The oligomer cracking unit to produce isobutylene is an improvement over tert-ether cracking in that there is no alcohol byproduct that could be a contaminant in the isobutylene product and would require additional purification, especially since alcohols are oxygenates which are PIB catalyst poisons. Also, the oligomer cracking unit, when integrated with a HR-PIB unit, can be used to crack byproduct oligomers and any off-specification HR-PIB product to isobutylene. The process also allows for a high value use of the low-value normal butylenes.

Typically, feedstocks for HR-PIB processes are isobutylene containing streams which do not contain normal butylenes. These streams can include high purity isobutylene containing 99+% isobutylene, isobutylene concentrate (IBC) containing 85-95% isobutylene with the balance being isobutane, dehydro effluent (DHE) containing 45-50% isobutylene with the balance being isobutane, and/or combinations of these streams with the corresponding intermediate isobutylene concentrations. However, these streams are not available in many parts of the world, thereby limiting the areas in which HR-PIB processes can be operated and limiting the commercial usefulness of the HR-PIB processes worldwide. In these and other areas, only CC4 and raffinate streams are available, and as discussed above, these streams contain low concentrations of isobutylene with the normal butylenes being the major components. The reaction of normal butylenes in the conventional HR-PIB process reduces the alpha vinylidene olefin isomer content such that the PIB produced is not true HR-PIB. Even if the conventional processes could be operated such that the normal butylenes do not react, the yield of HR-PIB based on the total feed stream is low. The current disclosure solves, at least, this problem.

In at least one embodiment, the C4 processing scheme described herein converts an amount of the normal butylenes in the crude C4 feedstock to isobutylene. In some embodiments, the conversion of normal butylenes to isobutylene can be greater than about 5%, such as from about 10% to about 100%, such as from about 15% to about 95%, such as from about 20% to about 85%, such as from about 25% to about 80%, such as from about 30% to about 75%, such as from about 35% to about 70%, such as from about 40% to about 65%, such as from about 45% to about 60%, such as from about 50% to about 55%, based on an amount of normal butylenes in the crude C4 feedstock. In some embodiments, the conversion of normal butylenes to isobutylene can be greater than about 90%, such as about 91%, such as about 92%, such as about 93%, such as about 94%, such as about 95%, such as about 96%, such as about 97%, such as about 98%, such as about 99%, such as about 100%, based on the amount of normal butylenes in the crude C4 feedstock. The conversion of normal butylenes to isobutylene may be such that all, or essentially all, of the normal butylenes in the crude C4 feedstock are converted to isobutylene, based on the amount of normal butylenes in the crude C4 feedstock.

In at least one embodiment, a conversion of a total butylenes content in a crude C4 feedstock to a high purity isobutylene can be greater than about 5%, such as from about 10% to about 100%, such as from about 15% to about 95%, such as from about 20% to about 85%, such as from about 25% to about 80%, such as from about 30% to about 75%, such as from about 35% to about 70%, such as from about 40% to about 65%, such as from about 45% to about 60%, such as from about 50% to about 55%, based on a total butylenes content in the crude C4 feedstock. The total butylenes content can include normal butylenes, isobutylene, or a combination thereof. In some embodiments, the conversion of a total butylenes content in a crude C4 feedstock to a high purity isobutylene can be greater than about 90%, such as about 91%, such as about 92%, such as about 93%, such as about 94%, such as about 95%, such as about 96%, such as about 97%, such as about 98%, such as about 99%, such as about 100%, based on the total butylenes content in the C4 feedstock.

In at least one embodiment, a conversion of a total butylenes content in a crude C4 feedstock to HR-PIB can be greater than about 5%, such as from about 10% to about 100%, such as from about 15% to about 95%, such as from about 20% to about 85%, such as from about 25% to about 80%, such as from about 30% to about 75%, such as from about 35% to about 70%, such as from about 40% to about 65%, such as from about 45% to about 60%, such as from about 50% to about 55%, based on a total butylenes content in the C4 feedstock. The total butylenes content can include normal butylenes, isobutylene, or a combination thereof. In some embodiments, the conversion of a total butylenes content in a crude C4 feedstock to HR-PIB can be greater than about 90%, such as about 91%, such as about 92%, such as about 93%, such as about 94%, such as about 95%, such as about 96%, such as about 97%, such as about 98%, such as about 99%, such as about 100%, based on the total butylenes content in the C4 feedstock.

In some embodiments, the present disclosure provides a process such that all, or essentially all, of the butylenes in a crude C4 byproduct stream from a steam cracker producing ethylene and propylene, can be converted to isobutylene. In at least one embodiment, the C4 processing schemes described herein can be integrated with a steam cracking unit in an olefin plant and operated at the olefin plant site.

In at least one embodiment, a HR-PIB unit can be integrated with a C4 processing unit utilizing the isobutylene output as a feedstock for the HR-PIB unit. The oligomeric byproducts from the HR-PIB unit can be cycled back to the C4 processing unit as a feed make-up to regenerate isobutylene. The net result can be that all, or nearly all, of the butylenes in a crude C4 stream from a steam cracker unit can be converted with 100%, or near 100%, selectivity to HR-PIB.

In at least one embodiment, the butadiene in a crude C4 stream can be concentrated as a side stream. This concentrated butadiene stream can be used for further processing, such as at an off-site or on-site extraction facility.

Feedstocks for the C4 Conversion

In some embodiments, the feedstock can include any feedstock containing butylenes, e.g., normal butylenes, isobutylene, and a combination thereof. Such feedstocks can include those feedstocks obtained from the cracking of hydrocarbons, such as naptha, gas oils, and lighter hydrocarbons. The feedstocks can include, e.g., crude C4 streams, raffinate-1, or raffinate-2. The feedstocks can contain 1,3-butadiene, 1,2-butadiene, isobutylene, 1-butene, 2-butenes (e.g., cis- and trans-2-butene), n-butane, isobutane, and a combination thereof. In at least one embodiment, the feedstocks can contain minor amounts of isobutylene (e.g., less than 10 wt %).

In at least one embodiment, the feedstock can include about 1 wt % or more normal butylenes, such as from about 3 wt % to about 100 wt %, such as 5 wt % to about 95 wt %, such as 10 wt % to about 90 wt %, such as 15 wt % to about 85 wt %, such as 20 wt % to about 80 wt %, such as 25 wt % to about 75 wt %, such as 30 wt % to about 70 wt %, such as 35 wt % to about 65 wt %, such as 40 wt % to about 60 wt %, such as 45 wt % to about 55 wt %, based on a total weight of the feedstock. In some embodiments, the feedstock can consist essentially of normal butylenes.

In at least one embodiment, the feedstock can include about 1 wt % or more of isobutylene, such as from about 3 wt % to about 100 wt %, such as 5 wt % to about 95 wt %, such as 10 wt % to about 90 wt %, such as 15 wt % to about 85 wt %, such as 20 wt % to about 80 wt %, such as 25 wt % to about 75 wt %, such as 30 wt % to about 70 wt %, such as 35 wt % to about 65 wt %, such as 40 wt % to about 60 wt %, such as 45 wt % to about 55 wt %, based on a total weight of the feedstock. In some embodiments, the feedstock can include about 5 wt % or less of isobutylene, such as from about 0 wt % to about 4 wt %, such as from about 0.1 wt % to about 2 wt %, such as from about 0.5 wt % to about 1 wt %. In some embodiments, the feedstock can consist essentially of isobutylene.

In at least one embodiment, the feedstock can include at least about 80 wt % isobutylene (for example, at least about 90 wt %, such as at least about 99 wt %) with the balance being isobutane and minor amounts of C3, normal butanes, butylenes, and butadiene. This feedstock can also be suitable for production of HR-PIB.

Example feedstocks include raffinate-1. The actual composition of raffinate-1 can be variable depending on the source. A typical raffinate-1 feedstock might contain about 0.5 wt % C3, about 4.5 wt % isobutane, about 16.5 wt % n-butane, about 38.5 wt % 1-butene, about 28.3 wt % isobutylene, about 10.2 wt % cis- and trans-2-butene, less than about 0.5 wt % butadiene, and less than about 1.0 wt % oxygenates. Other examples of raffinate-1 feedstocks also include those provided in Table 1.

In at least one embodiment, the feedstock may include alkanes and isoalkanes, such as C2 to C40 alkanes and C2 to C40 isoalkanes.

TABLE 1

Examples of Raffinate-1 Feedstocks

| Composition | Ex. 1 (wt %) | Ex. 2 (wt %) | Ex. 3 (wt %) | Ex. 4 (wt %) |
|---|---|---|---|---|
| C3 | 0.5 | — | 4.0 | 0.6 |
| isobutane | 4.5 | 14.0 | 25.0 | 4.4 |
| n-butane | 16.5 | 7.0 | 13.0 | 16.7 |
| 1-butene | 38.5 | 45.0 | 15.0 | 30.0 |
| isobutylene | 28.3 | 22.0 | 15.0 | 37.2 |

TABLE 1-continued

Examples of Raffinate-1 Feedstocks

| Composition | Ex. 1 (wt %) | Ex. 2 (wt %) | Ex. 3 (wt %) | Ex. 4 (wt %) |
|---|---|---|---|---|
| cis-2-butene | 10.2 (total of cis and trans isomers) | 6.7 | 15.5 | 2.3 |
| trans-2-butene |  | 5.0 | 12.0 | 8.4 |
| butadiene | 0.5 | 0.3 | 0.5 | 0.4 |

Amounts provided are approximate values.

Another feedstock that can be used is an effluent from a dehydrogenation of isobutane to isobutylene. Typically, such effluents can contain from about 42 wt % to about 45 wt % isobutylene, or from about 50 wt % to about 52 wt % isobutane, with the balance being C3, normal butanes, normal butylenes, and butadiene. This feedstock can be used when unreactive isobutane may be utilized, for example, in cooperation with an isobutane dehydrogenation unit.

When using any feedstock, any unreacted portion of the feedstock may be recycled through various parts of the processing schemes described herein.

Processes

A C4 conversion process is described in which the normal butylenes in a crude C4, raffinate, and any other butylenes-containing streams can be converted to isobutylene and the C4 conversion process can be integrated with an HR-PIB process.

FIG. 1 is a flow diagram of a method 100 of processing C4 according to some embodiments. Generally, it is a method of converting a feed according to some embodiments.

The method can be performed in a C4 processing unit. The method can include performing an oligomerization operation 105 by introducing a feed to an oligomerization catalyst in an oligomerization reactor to form a first reactor effluent. The first reactor effluent can include one or more oligomers of isobutylene (e.g., diisobutylene, triisobutylene, tetraisobutylene, and a combination thereof). The feed can be any feedstock discussed above for the C4 conversion, such as a feed containing isobutylene. The oligomerization operation can be selective for converting isobutylene to the oligomers of isobutylene, while the normal butylenes (e.g., 1-butene, cis-2-butene, and trans-2-butene) do not react.

In some embodiments, the oligomerization operation 105 can be performed by an appropriate oligomerization operation known to those of skill in the art. Suitable catalysts for the oligomerization operation can be an acidic catalyst, such as a solid acid catalyst, such as an acidic ion exchange resin compound, for example Amberlyst sulfonic acid resins. As an example, the oligomerization operation 105 may be performed by the following prophetic procedure. A process stream containing isobutylene, which can also contain butanes and other butylene isomers, is passed through a fixed bed of acidic ion exchange resin, such as Amberlyst 15, at a temperature of from about 50° C. to about 150° C. and at an liquid hourly space velocity (LHSV) of from about 1 $h^{-1}$ to about 5 $h^{-1}$. In some embodiments, the oligomerization operation 105 can convert a feed containing isobutylene to a post-oligomerization mixture (e.g., the first reactor effluent) containing oligomers of isobutylene at a conversion of about 1% or more, such as about 5% or more, such as from about 10% to about 100%, such as from about 15% to about 95%, such as from about 20% to about 85%, such as from about 25% to about 80%, such as from about 30% to about 75%, such as from about 35% to about 70%, such as from about 40% to about 65%, such as from about 45% to about 60%, such as from about 50% to about 55%, based on an amount of isobutylene in the feed. In some embodiments, the conversion of the feed containing isobutylene to the oligomers of isobutylene can be greater than about 90%, such as about 91%, such as about 92%, such as about 93%, such as about 94%, such as about 95%, such as about 96%, such as about 97%, such as about 98%, such as about 99%, such as about 100%, based on the amount of isobutylene in the feed.

The method 100 can further include performing a first distillation operation 110 by introducing the first reactor effluent to a first distillation unit to form a first distillation effluent and a second distillation effluent. The first distillation effluent can include normal butylenes, alkanes, butadienes, or a combination thereof, and the second distillation effluent can include one or more oligomers of isobutylene. The first distillation operation allows for separation of the normal butylenes and other material from the oligomers of isobutylene.

In some embodiments, the first distillation operation 110 can be performed by an appropriate distillation operation known to those of skill in the art. For example, the distillation operation 110 may be performed in a distillation column at a temperature of from about 50° C. to about 100° C. and a pressure of from about 50 psi to about 100 psi. In some embodiments, the distillation operation 110 to forms second distillation effluent containing isobutylene oligomers. The amount of isobutylene oligomers in the second distillation effluent can be about 1 wt % or more, such as about 5 wt % or more, such as from about 10 wt % to about 100 wt %, such as from about 15 wt % to about 95 wt %, such as from about 20 wt % to about 85 wt %, such as from about 25 wt % to about 80 wt %, such as from about 30 wt % to about 75 wt %, such as from about 35 wt % to about 70 wt %, such as from about 40 wt % to about 65 wt %, such as from about 45 wt % to about 60 wt %, such as from about 50 wt % to about 55 wt %, based on a weight of the second distillation effluent. In some embodiments, the amount of isobutylene oligomers in the second distillation effluent can be greater than about 90 wt %, such as about 91 wt %, such as about 92 wt %, such as about 93 wt %, such as about 94 wt %, such as about 95 wt %, such as about 96 wt %, such as about 97 wt %, such as about 98 wt %, such as about 99 wt %, such as about 100 wt %, based on the weight of the second distillation effluent.

The method 100 can further include performing a cracking operation 115 by introducing the second distillation effluent to a cracking reactor to form a cracking reactor effluent. The cracking reactor effluent can include a high purity isobutylene. The cracking operation 115 serves to crack the isobutylene oligomers into a mixture that includes isobutylene (e.g., high purity isobutylene).

In some embodiments, the cracking operation 115 can be performed by an appropriate cracking operation known to those of skill in the art. Suitable catalysts for the cracking operation include metal oxides, such as gamma-alumina; activated metal oxides, such as solid $BF_3$ metal oxide complexes; zeolites, such as Y-zeolites; or activated zeolites. As an example, the cracking operation 115 may be performed by the following prophetic procedure. A process stream containing isobutylene oligomers, such as dimers, trimers, tetramers, and a combination thereof, is passed over a magnesium silicate catalyst contained in a suitable fixed bed reactor. The reactor conditions can include a temperature of from about 250° C. to about 450° C., a pressure of about atmospheric pressure, and a LHSV of from about 1 $h^{-1}$ to about 5 h$^{-1}$. The process stream containing isobutylene oligomers can be diluted with an inert gas such as nitrogen to a volume percent of from about 10 vol % to about 90 vol %.

In some embodiments, the cracking operation 115 can convert a mixture containing oligomers of isobutylene to cracking reactor effluent containing isobutylene (e.g., high purity isobutylene) at a conversion of about 1% or more, such as about 5% or more, such as from about 10% to about 100%, such as from about 15% to about 95%, such as from about 20% to about 85%, such as from about 25% to about 80%, such as from about 30% to about 75%, such as from about 35% to about 70%, such as from about 40% to about 65%, such as from about 45% to about 60%, such as from about 50% to about 55%, based on an amount of oligomers of isobutylene introduced to a cracking reactor. In some embodiments, the conversion of the oligomers to isobutylene can be greater than about 90%, such as about 91%, such as about 92%, such as about 93%, such as about 94%, such as about 95%, such as about 96%, such as about 97%, such as about 98%, such as about 99%, such as about 100%, based on an amount of oligomers of isobutylene introduced to a cracking reactor.

The method 100 can further include performing an isomerization operation 120 by introducing the first distillation effluent to an isomerization reactor to form an isomerized product effluent. The isomerized product effluent can be enriched in isobutylene. The isomerization operation 120 can be a skeletal isomerization. The isomerization operation can involve a stream that contains normal butylenes (e.g., 1-butene, cis-2-butene, trans-2-butene, and combinations thereof). This stream may also contain isobutylene. At high temperatures and in the presence of a catalyst, the normal butylenes and isobutylene can reach a chemical equilibrium such that the amount of isobutylene can be maximized.

In some embodiments, the isomerization operation 120 can be performed by an appropriate isomerization operation known to those of skill in the art. For example, the isomerization operation 120 may be performed by the following prophetic procedure. A stream of normal butylenes, containing 1-butene, cis-2-butene, and trans-2-butene, and only minor amounts of isobutylene is passed over a reactor bed containing a zeolite catalyst, such as a boron beta-zeolite. The reactor conditions can include a temperature of from about 450° C. to about 500° C., a pressure of about atmospheric pressure, and a LHSV of from about 4 h$^{-1}$ to about 5 h$^{-1}$, such that the reaction is in the vapor phase. The butylenes vapors can be diluted with nitrogen at a weight ratio of from about 1.4 to about 1.5. Selectivity to isobutylene can be greater than about 50%.

In some embodiments, the isomerization operation 120 can convert a mixture containing one or more normal butylenes to an isomerized product effluent containing isobutylene at a conversion of about 1% or more, such as about 5% or more, such as from about 10% to about 100%, such as from about 15% to about 95%, such as from about 20% to about 85%, such as from about 25% to about 80%, such as from about 30% to about 75%, such as from about 35% to about 70%, such as from about 40% to about 65%, such as from about 45% to about 60%, such as from about 50% to about 55%, based on a total amount of normal butylenes introduced to the isomerization reactor. In some embodiments, the isomerization can have a conversion of greater than about 90%, such as about 91%, such as about 92%, such as about 93%, such as about 94%, such as about 95%, such as about 96%, such as about 97%, such as about 98%, such as about 99%, such as about 100%, based on the total amount of normal butylenes introduced to the isomerization reactor.

In at least one embodiment, the method 100 can further include combining the isomerized product effluent with the feed comprising isobutylene (e.g., the feed that enters the C4 processing unit), and introducing the isomerized product effluent to the oligomerization reactor to undergo an oligomerization operation. This oligomerization operation can be similar to the oligomerization operation 105.

In at least one embodiment, the method 100 can include performing an optional purge operation to remove butadienes (e.g., 1,3-butadiene and 1,2-butadiene) and optionally non-reactive butanes from the isomerized product effluent. Other materials such as alkanes (e.g., butanes) may also be removed during this purge operation or another optional purge operation. Thus, before purging, the pre-purge stream can include alkanes, butadienes, 1-butene, 2-butene, isobutylene, and a combination thereof. After the optional purge operation, the post-purge stream can contain 1-butene, 2-butene, isobutylene, and a combination thereof. In some embodiments, the optional purge operation can be performed by any appropriate purge operation known to those of skill in the art. For example, the purge operation may be operated by adjusting a valve to a pre-determined purge flow rate. The purge flow rate can be from about 1% to about 35% of the flow rate of an effluent exiting the isomerization reactor. The purge flow rate can be adjusted based on the amount of butadiene, unreactive butanes, or a combination thereof in the feed that enters the method 100. Alternatively, the purge flow rate can be adjusted based on the amount of butadiene, unreactive butanes, or a combination thereof in the isomerized product effluent. For example, if the isomerized product effluent is flowing at a flow rate of about 200 gallons/min, the purge flow rate can be operated at 10% of that which is about 20 gallons/min.

In at least one embodiment, the method 100 can further include performing an optional second distillation operation prior to the cracking operation 115. The optional second distillation operation can be used to separate diisobutylene from the other oligomers of isobutylene in the stream flowing from the first distillation unit in the distillation operation 110. The optional second distillation operation may be performed by introducing the second distillation effluent to a second distillation unit prior to the cracking reactor to form a third distillation effluent and a fourth distillation effluent. The third distillation effluent can include oligomers other than diisobutylene and the third distillation effluent can be introduced to the cracking reactor. The fourth distillation effluent can include diisobutylene. In cases where there is not a need to separate the diisobutylene, the oligomers of isobutylene (including diisobutylene) produced from the first distillation operation 110 can be used directly for the cracking operation 115.

In some embodiments, the optional second distillation operation can be performed by an appropriate purge operation known to those of skill in the art. For example, the optional second distillation operation may be performed in a distillation column at a temperature of from about 100° C. to about 150° C. and a pressure of from about ambient pressure to about 25 psi.

In some embodiments, the optional second distillation operation of the mixture containing oligomers of isobutylene produces a third distillation effluent. The amount of oligomers in the third distillation effluent can be about 1% or more, such as about 5% or more, such as from about 10% to about 100%, such as from about 15% to about 95%, such as from about 20% to about 85%, such as from about 25% to about 80%, such as from about 30% to about 75%, such as from about 35% to about 70%, such as from about 40% to about 65%, such as from about 45% to about 60%, such as from about 50% to about 55%, based on a total amount of oligomers of isobutylene introduced to the optional second distillation operation. In some embodiments, the amount of oligomers in the third distillation effluent can be greater than about 90%, such as about 91%, such as about 92%, such as about 93%, such as about 94%, such as about 95%, such as about 96%, such as about 97%, such as about 98%, such as about 99%, such as about 100%, based on the total amount of oligomers of isobutylene introduced to the optional second distillation operation.

Figure 4:
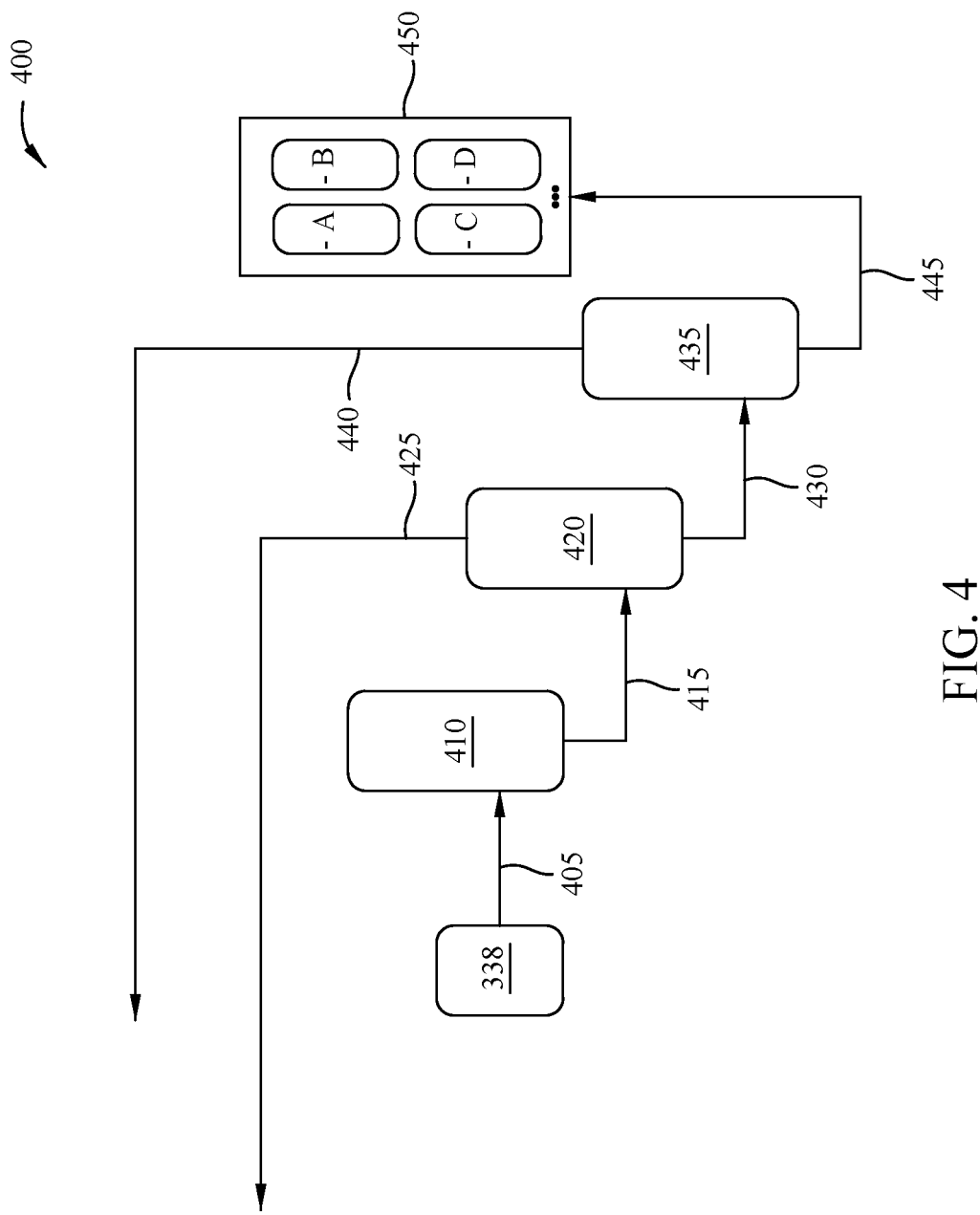
FIG. 4 is a HR-PIB processing according to some embodiments.

In some embodiments, the method 100 can further include performing an optional polishing operation to further purify the high purity isobutylene stream flowing from the cracking operation 115. The optional polishing operation can be accomplished by introducing the cracking reactor effluent to a polishing column to form a first polishing column effluent and a second polishing column effluent. The first polishing column effluent can include the high purity isobutylene. The second polishing column effluent is an impurity stream that can include various butylenes including normal butylenes and isobutylene. The high purity isobutylene can be used for further operations such as polymerization (as shown in FIG. 4) and/or chemical derivatization.

In some embodiments, the optional polishing operation can be performed by an appropriate polishing operation known to those of skill in the art. For example, the optional polishing operation may be performed by the following prophetic conditions. The effluent from the oligomer cracking unit (or another stream entering the polishing column) is passed through a distillation column operating at WHSV of from about 1 $h^{-1}$ to about 5 $h^{-1}$, column temperature of from about 25° C. to about 100° C. and a column pressure of from about 25 psi to 100 psi.

In some embodiments, the optional polishing operation can convert the mixture containing isobutylene (which may be high purity isobutylene) to a first polishing column effluent that includes an isobutylene of higher purity. The amount of high purity isobutylene in the post-polishing mixture can be about 1 wt % or more, such as about 5 wt % or more, such as from about 10 wt % to about 100 wt %, such as from about 15 wt % to about 95 wt %, such as from about 20 wt % to about 85 wt %, such as from about 25 wt % to about 80 wt %, such as from about 30 wt % to about 75 wt %, such as from about 35 wt % to about 70 wt %, such as from about 40 wt % to about 65 wt %, such as from about 45 wt % to about 60 wt %, such as from about 50 wt % to about 55 wt %, based on a total amount of first polishing column effluent. In some embodiments, the amount of high purity isobutylene in the post-polishing mixture can be greater than about 90 wt %, such as about 91 wt %, such as about 92 wt %, such as about 93 wt %, such as about 94 wt %, such as about 95 wt %, such as about 96 wt %, such as about 97 wt %, such as about 98 wt %, such as about 99 wt %, such as about 100 wt %, based on the total amount of first polishing column effluent.

In at least one embodiment, the method 100 can further include combining the second polishing column effluent with the feed comprising isobutylene (e.g., the feed that enters the C4 processing unit); and introducing the second polishing column effluent to the oligomerization reactor to undergo an oligomerization operation. This oligomerization operation can be similar to the oligomerization operation 105.

In some embodiments, the raw materials for each operation can be recirculated one or more times through one or more operations of the method. For example, in at least one embodiment, any isobutylene that did not oligomerize to isobutylene oligomers during the oligomerization operation 105 can undergo another oligomerization operation, and the oligomerization operation can be repeated one or more times. Similarly, the starting materials and/or byproducts of operations 110-120 (as well as operation 105) can be fed, either directly or indirectly, back through one or more of operations of the method 100. By recirculating the starting materials and/or byproducts back through one or more operations of the method 100, higher and higher amounts of desired product can be obtained. In addition, the products of the individual operations can be removed to undergo a subsequent operation until the desired product stream is obtained. By removing the products from these individual processes, higher and higher amounts of product can be obtained. In addition, recycling the convertible components to isobutylene can serve to increase the selectivity to isobutylene to 100% or near 100%.

Figure 2:
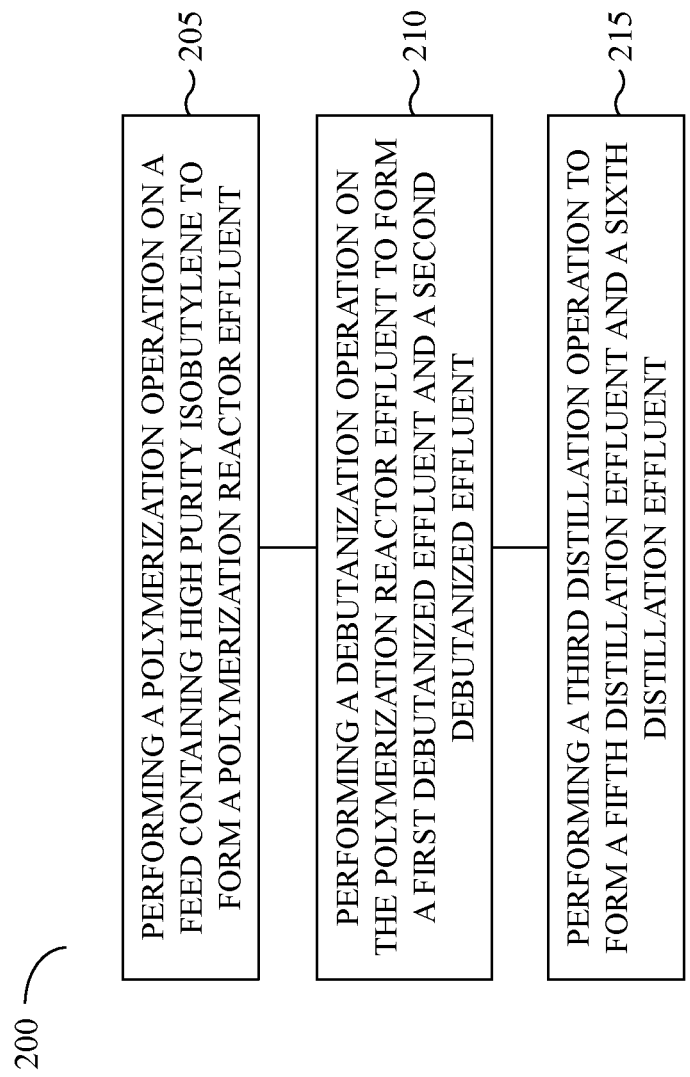
FIG. 2 is a flow diagram flow diagram for a HR-PIB processing method according to some embodiments.

FIG. 2 is a flow diagram for a HR-PIB processing method 200 according to some embodiments. In some embodiments, the method 200 can be integrated with the method 100 such that the C4 processing method includes an HR-PIB process.

The method 200 can include performing a polymerization operation 205 on a feed that includes high purity isobutylene. The polymerization operation 205 may be performed by introducing a feed that includes high purity isobutylene, e.g., the cracking reactor effluent, the first polishing column effluent, or a combination thereof, to a polymerization reactor to form a polymerization reactor effluent. The polymerization reactor effluent can include a polyisobutylene, e.g., a HR-PIB, and impurities. Thus, the polymerization forms a crude polyisobutylene, such as a crude HR-PIB. In some embodiments, the polymerization operation 205 to form polyisobutylene can be performed by an appropriate polymerization operation known to those of skill in the art. For example, the polymerization may be performed according to PCT Publication No. 2018/018808, the entirety of which is incorporated by reference.

In at least one embodiment, the polymerization occurs in the presence of a solid dispersible $BF_3$ complex catalyst and/or in a high-speed reactor, such as a fast reactor. As an example, the polymerization operation 205 may be performed by the following prophetic procedure. High purity isobutylene is fed to a tubular loop reactor and slurried in situ with a solid $BF_3$ complex catalyst such that the catalyst concentration is in the range of from about 2,000 ppm to about 1,000 ppm. The reaction temperature is varied depending on the desired molecular weight, but in general the reaction temperature is greater than about 0° C. The residence time in the reactor is less than about 4 minutes. The crude HR-PIB effluent can then be purified by a first filtration in a filtration unit to remove the catalyst.

In some embodiments, the polymerization operation 205 can convert the mixture containing isobutylene (e.g., high purity isobutylene) to a polymerization reactor effluent containing polyisobutylene (e.g., HR-PIB) at a conversion of about 1% or more, such as about 5% or more, such as from about 10% to about 100%, such as from about 15% to about 95%, such as from about 20% to about 85%, such as from about 25% to about 80%, such as from about 30% to about 75%, such as from about 35% to about 70%, such as from about 40% to about 65%, such as from about 45% to about 60%, such as from about 50% to about 55%, based on an amount of isobutylene undergoing the polymerization operation. In some embodiments, the conversion of isobutylene to polyisobutylene can be greater than about 90%, such as about 91%, such as about 92%, such as about 93%, such as about 94%, such as about 95%, such as about 96%, such as about 97%, such as about 98%, such as about 99%, such as about 100%, based on an amount of isobutylene undergoing the polymerization operation.

The method 200 can further include a debutanization operation 210 to remove unreacted isobutylene from the crude HR-PIB. The debutanization operation 210 can be performed by introducing the polymerization reactor effluent to a debutanizer column to form a first debutanized effluent and a second debutanized effluent. The first debutanized effluent can include the HR-PIB and optionally oligomer byproducts, and the second debutanized effluent can include isobutylene (e.g., a high purity isobutylene). The debutanizer column can be a debutanizer fractionator, such as a fractional distillation column. In some embodiments, the debutanization operation 210 can be performed by an appropriate debutanization operation known to those of skill in the art. For example, the debutanization operation 210 may be performed with the following prophetic conditions. The effluent from the HR-PIB reactor unit is passed through a distillation column operating at WHSV of from about 1 $h^{-1}$ to about 60 $h^{-1}$ or more, at a column temperature of from about 25° C. to about 100° C., and a column pressure of from about 25 psi to about 100 psi.

In some embodiments, the amount of HR-PIB in the first debutanized effluent can be about 1 wt % or more, such as about 5 wt % or more, such as from about 10 wt % to about 100 wt %, such as from about 15 wt % to about 95 wt %, such as from about 20 wt % to about 85 wt %, such as from about 25 wt % to about 80 wt %, such as from about 30 wt % to about 75 wt %, such as from about 35 wt % to about 70 wt %, such as from about 40 wt % to about 65 wt %, such as from about 45 wt % to about 60 wt %, such as from about 50 wt % to about 55 wt %, based on a total amount of first debutanized effluent. In some embodiments, the amount of HR-PIB in the first debutanized effluent can be greater than about 90 wt %, such as about 91 wt %, such as about 92 wt %, such as about 93 wt %, such as about 94 wt %, such as about 95 wt %, such as about 96 wt %, such as about 97 wt %, such as about 98 wt %, such as about 99 wt %, such as about 100 wt %, based on the total amount of first debutanized effluent.

In at least one embodiment, the method 200 can further include a third distillation operation 215 to remove oligomeric byproducts formed during the polymerization operation 205. The third distillation operation 215 can be performed by introducing the first debutanized effluent to a third distillation unit to form a fifth distillation effluent and a sixth distillation effluent. The fifth distillation effluent can include the HR-PIB and the sixth distillation effluent can include the oligomer byproducts.

In some embodiments, the third distillation operation 215 can be performed by an appropriate distillation operation known to those of skill in the art. For example, the distillation operation 215 may be performed in a distillation column at a temperature of from about 200° C. to about 250° C., at a pressure of from about 1 mm Hg to about 100 mm Hg.

In some embodiments, the amount of HR-PIB in the fifth distillation effluent can be about 1 wt % or more, such as about 5 wt % or more, such as from about 10 wt % to about 100 wt %, such as from about 15 wt % to about 95 wt %, such as from about 20 wt % to about 85 wt %, such as from about 25 wt % to about 80 wt %, such as from about 30 wt % to about 75 wt %, such as from about 35 wt % to about 70 wt %, such as from about 40 wt % to about 65 wt %, such as from about 45 wt % to about 60 wt %, such as from about 50 wt % to about 55 wt %, based on a total amount of fifth distillation effluent. In some embodiments, the amount of HR-PIB in the fifth distillation effluent can be greater than about 90 wt %, such as about 91 wt %, such as about 92 wt %, such as about 93 wt %, such as about 94 wt %, such as about 95 wt %, such as about 96 wt %, such as about 97 wt %, such as about 98 wt %, such as about 99 wt %, such as about 100 wt %, based on the total amount of fifth distillation effluent.

The oligomer byproducts in the sixth distillation effluent can be back-cracked in a cracking operation. Thus, and in at least one embodiment, the method 200 can further include combining the sixth distillation effluent with the second distillation effluent (e.g., the feed that enters the cracking reactor), the third distillation effluent (e.g., another feed that enters the cracking reactor), or a combination thereof; and introducing the sixth distillation effluent to the cracking reactor to undergo a cracking operation. This cracking operation can be similar to the cracking operation 115.

In addition, the second debutanized effluent, which can contain isobutylene, can be recycled to the polishing column of the polishing operation in method 100. Thus, and in at least one embodiment, the method 200 can include combining the second debutanized effluent with the cracking reactor effluent, and introducing the second debutanized effluent to the polishing column to undergo a polishing operation.

In at least one embodiment, any isobutylene that did not polymerize during the polymerization operation 205 can undergo another polymerization operation, and the polymerization operation can be repeated one or more times. Similarly, the starting materials and/or byproducts of 205-215 can be fed, either directly or indirectly, back through one or more of operations of the method 200. When the C4 processing method is integrated with the HR-PIB process, the starting materials and byproducts from various operations of the method 200 can be re-circulated to operations of the method 100 in order to increase the amount of desired product stream obtained, as discussed above. Product removal, as discussed above, can further aid in driving the various operations closer and closer to completion. In addition, recycling the unreacted isobutylene within the polymerization operation and any byproducts recycled back to operations in method 100 serves to can serve to increase the selectivity of isobutylene to HR-PIB (PIB) to 100% or near 100%.

Moreover, the byproducts of the individual operations can be recirculated to different parts of the method. By recirculating byproducts to various parts of the method, the reactions and process are driven to completion (or near completion). For example, and in at least one embodiment, the products of the isomerization operation 120 can be fed to the crude C4 stream that undergoes oligomerization operation 105. As more and more of the isobutylene is removed by the oligomerization, more and more isobutylene is formed in the isomerization process. Similarly, and in at least one embodiment, the impurity stream containing various butylenes that is removed in the optional polishing operation can be recirculated back to the crude C4 stream that undergoes the oligomerization operation 105. In at least one embodiment, the unreacted isobutylene removed during the debutanization operation 210 can be recirculated back into the isobutylene stream that undergoes the optional polishing operation. In at least one embodiment, the undesired oligomers that are removed during distillation operation 215 can be recirculated back into the oligomers stream that undergoes the cracking operation 115 and/or optional, second distillation operation. As more and more of the byproducts and unreacted materials from certain operations are recirculated to different operations of the method, more and more desired products (e.g., high purity isobutylene and HR-PIB) can form.

Conventional methods of making isobutylene utilize alcohols (e.g., methanol) to convert raffinate streams to ethers (e.g., MTBE) and a subsequent back-cracking of the ether to make isobutylene and alcohol. These conventional methods suffer from using and producing alcohols and oxygenates in the process. Alcohols and oxygenates are detrimental impurities in isobutylene, particularly when the isobutylene is used to produce polyisobutylene. In contrast, the process described herein advantageously avoids the use of alcohols. This is a technological and economical improvement over conventional processes. The process described herein is more cost-efficient and cleaner, and can convert all, or nearly all, of the normal butylenes in a C4 containing feedstock to isobutylenes with high purity. Conventional methods cannot do this. In contrast to conventional methods, the process described herein can also convert all, or nearly all, of the normal butylenes in a C4 containing feedstock to polyisobutylene and HR-PIB.

Figure 3:
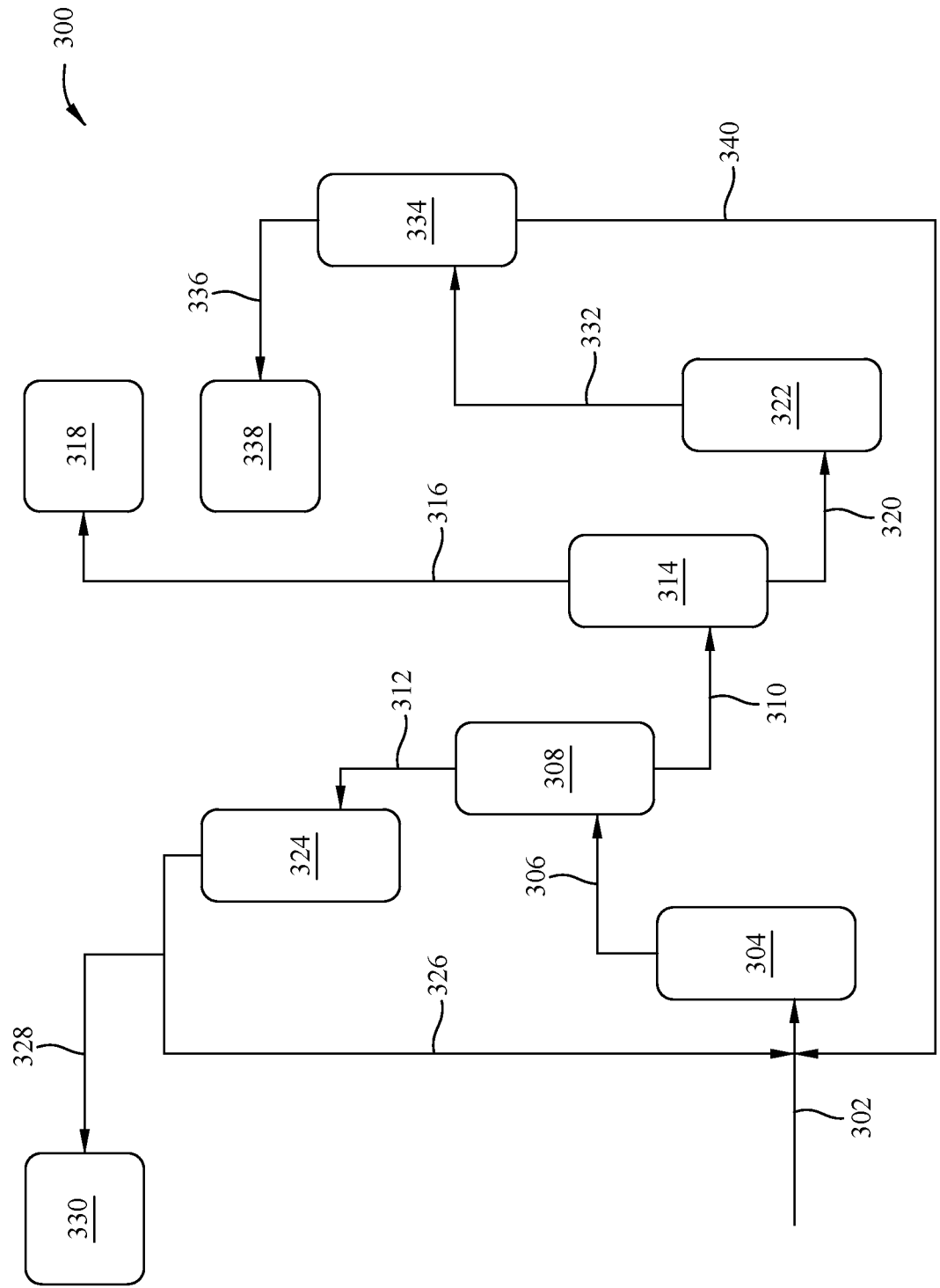
FIG. 3 is a C4 processing unit according to some embodiments.

FIG. 3 is a C4 processing unit 300 for carrying out certain aspects of the present disclosure according to some embodiments. More generally, a configuration shown in FIG. 3 or similar to FIG. 3 can be used for forming high purity isobutylene of the present disclosure according to some embodiments. The C4 processing unit 300 can convert at least a portion of the normal butylenes (e.g., 1-butene, cis-2-butene, and trans-2-butene) in a feedstock (e.g., a C4 stream) to isobutylene (e.g., a high purity isobutylene). In at least one embodiment, the C4 processing unit can 300 convert all, or nearly all, of the normal butylenes in the feedstock to isobutylene (e.g., a high purity isobutylene). In at least one embodiment, the feedstock can be a crude C4 (CC4) stream from an olefin plant.

Referring to FIG. 3, a feedstock can enter the C4 processing unit 300 through a feed line. The feed line 302 is coupled to an oligomerization reactor 304, e.g., a catalytic selective oligomerization reactor. During use, a feedstock of the feed line 302 can include an isobutylene containing feed such as raffinate-1, raffinate-2, CC4, or any other butylenes containing stream. The isobutylene in the feedstock can be selectively oligomerized in the presence of an oligomerization catalyst to isobutylene oligomers such as dimers and higher oligomers of isobutylene such as trimers and tetramers of isobutylene. The normal butylenes and/or butadienes in the feedstock do not react in the oligomerization reactor 304. The oligomerization reactor 304 can be coupled to a distillation unit 308. The oligomerization reactor effluent containing the crude isobutylene oligomers, normal butylenes, and/or butadienes can be directed to the distillation unit 308 via a line 306. The distillation unit 308 can separate the oligomers of isobutylene from the other components, e.g., the normal butylenes and butadienes.

The distillation unit 308 can be coupled to a cracking reactor 322 and to an isomerization unit/reactor, e.g., a skeletal isomerization reactor. The isomerization reactor can also be coupled to the feed line 302.

A first distillation effluent, e.g., distillation overheads, such as normal butylenes and/or butadienes, can be directed out of the distillation unit 308 via a line 312. A second distillation effluent, e.g., distillation bottoms such as the isobutylene oligomers, can be flowed directly out of the distillation unit 308 via a line 310 to the cracking reactor 322. The cracking reactor 322 can be a catalytic distillation cracking reactor. Alternatively, and in embodiments where an optional distillation unit is located at a point between distillation unit 308 and cracking reactor 322, the second distillation effluent can be directed to an optional distillation unit 314 where diisobutylene (dimer of isobutylene) can be separated from the other isobutylene oligomers. This optional distillation unit 314 may be used, e.g., when there is a demand for diisobutylene (DIB). Effluents from the optional distillation unit 314 include a third distillation effluent and a fourth distillation effluent. In applications where DIB is separated, the fourth distillation effluent contains DIB and can be fed to a DIB storage tank 318 through a line 316, and the third distillation effluent containing the other isobutylene oligomers can be directed to a cracking reactor 322 through a line 320. In cases where DIB is not removed from the distillation bottoms stream flowing out of distillation unit 308, the distillation bottoms can be flowed directly into the cracking reactor 322. Of note, the DIB storage tank 318 can be a pipeline, a tank truck, a rail car, or another suitable means to transport the DIB.

The first distillation effluent flowing out of the distillation unit 308 can be directed to an isomerization reactor 324. The first distillation effluent can contain mostly unreacted normal butylenes and low amounts of isobutylene. In the isomerization reactor 324, the first distillation effluent can be isomerized to an isomerized product effluent. The isomerized product effluent can be an equilibrium mixture where the amount of isobutylene is maximized. The isomerized product effluent (e.g., the equilibrium mixture enriched in isobutylene) can exit the isomerization reactor 324 via a line 326 and can be cycled back to the feedstock at the feed line 302, thereby re-entering the processing unit.

The butadiene in the C4 stream that enters the C4 processing unit 300 does not react in any of the unit operations and can build up in the various processes of the C4 processing unit 300. The butadiene can be purged from the processing unit through a line 328 that is coupled to line 326. The butadiene can be collected in a butadiene storage tank 330 that is coupled to line 328. Alternatively, the butadiene storage tank 330 can be a pipeline, a tank truck, a rail car, or another suitable means to transport the butadiene purge to a butadiene processing facility. The butadiene purge can be operated so as to concentrate the butadiene to a level that is commercially viable to be extracted by an on-site or off-site butadiene extraction facility.

With continuing reference to FIG. 3, the oligomers can be cracked to isobutylene, such as a high purity isobutylene, in the cracking reactor 322. The cracking reactor 322 can be coupled to a polishing column. The cracking reactor effluent, e.g., a stream containing the newly formed isobutylene, can be directed via line 332 to a polishing column 334. The polishing column can be coupled to a polymerization reactor of a HR-PIB processing unit (not shown), a high purity isobutylene storage tank 338, and/or the feed line 302.

The polishing column 334 can be used to further purify the isobutylene exiting the cracking reactor 322 to a high purity isobutylene. Effluents flowing from the polishing column 334 include a first polishing column effluent and a second polishing column effluent. The first polishing column effluent can contain the high purity isobutylene and the second polishing column effluent can contain various butylenes. The first polishing column effluent containing the high purity isobutylene can exit the polishing column 334 via line 336 and can be stored in the high purity isobutylene storage tank 338. Alternatively, a first polishing column effluent containing the high purity isobutylene can exit the polishing column and enter an HR-PIB processing unit as described below. The second polishing column effluent containing various butylenes can exit polishing column 334 via a line 340 and can be cycled back to the C4 stream at the line 302, thereby re-entering the C4 processing unit. Of note, the high purity isobutylene storage tank 338 can be a pipeline, a tank truck, a rail car, or another suitable means to transport the high purity isobutylene.

In some embodiments, a reactive distillation reactor can be used instead of the oligomerization reactor 304 and distillation unit 308. In some embodiments, a butadiene isomerization reactor may be added to the C4 processing unit in order to convert the butadienes contained in the C4 feedstock to normal butylenes. This can help prevent butadiene from building up in the processing unit. The butadiene isomerization reactor may be coupled to the butadiene storage tank 330 and to the feed line 302. However, it may be advantageous to allow butadiene to build up to some equilibrium level maintained by employing a butadiene purge stream. The butadiene purge stream can have commercial value as a feedstock to butadiene manufacturers and processors.

FIG. 4 is a HR-PIB processing unit 400 for carrying out certain aspects of the present disclosure according to some embodiments. More generally, a configuration shown in FIG. 4 or similar to FIG. 4 can be used for forming HR-PIB of the present disclosure according to some embodiments. As shown, the HR-PIB processing unit 400 can be integrated with a C4 processing unit according to some embodiments.

The HR-PIB processing unit 400 can utilize the produced isobutylene feedstock, e.g., the isobutylene stored in the high purity isobutylene storage tank 338 as a feedstock for HR-PIB production.

With reference to FIG. 4, a HR-PIB processing unit 400 may include a polymerization reactor (e.g., an HR-PIB reactor) 410 coupled to a unit containing a feed, the feed containing high purity isobutylene. The feed containing high purity isobutylene may enter the HR-PIB processing unit via line 405 and into the HR-PIB reactor 410. The HR-PIB reactor 410 can convert the feed containing the high purity isobutylene to a crude HR-PIB. The HR-PIB reactor 410 can be a high-speed, low residence time reactor such as a fast reactor. The feed containing high purity isobutylene can come from a storage tank, e.g., high purity isobutylene storage tank 338, and storage tank 338 can be coupled to the HR-PIB reactor. Alternatively, the feed containing high purity isobutylene can come from an isobutylene polishing column such as the polishing column 334, and thus polishing column 334 can be coupled to the HR-PIB reactor 410.

The HR-PIB reactor 410 can be coupled to a debutanizer 420. After the high purity isobutylene is polymerized in the HR-PIB reactor 410, a polymerization reactor effluent containing a crude HR-PIB can exit HR-PIB reactor 410 and be directed, via line 415, to a debutanizer column 420. The polymerization reactor effluent can contain oligomer byproducts and/or unreacted high purity isobutylene. The debutanizer column 420 can separate unreacted isobutylene from the crude HR-PIB. The debutanizer column can be operated at pressures of about 50 pounds per square inch gauge (psig) to about 100 psig. Effluents flowing from the debutanizer column 420 include a first debutanized effluent and a second debutanized effluent. The first debutanized effluent can include the HR-PIB and optionally oligomer byproducts, and the second debutanized effluent can include unreacted high purity isobutylene.

The debutanizer 420 can be coupled to the C4 processing unit 300 at the line 332. Thus, the second debutanized effluent containing unreacted isobutylene can be directed, via line 425, to a C4 processing unit and enter at the line 332 where it can then enter the polishing column 334. The debutanizer 420 can be coupled to a distillation unit 435 (an oligomeric distillation unit) via line 430 where oligomeric byproducts can be removed from the HR-PIB. Thus, the first debutanized effluent can be directed via line 430 to the distillation unit 435.

Effluents from the oligomer distillation unit 435 include a fifth distillation effluent and a sixth distillation effluent. The fifth distillation effluent can include the HR-PIB and the sixth distillation effluent can include oligomer byproducts. The oligomer distillation unit 435 can be coupled to the C4 processing unit at the line 310 and/or the line 320. Thus, the sixth distillation effluent containing the oligomer byproducts can be directed, via line 440, to a C4 processing unit and enter at line 320 or line 310, and then undergo a cracking operation to regenerate isobutylene.

The oligomer distillation unit 435 can be coupled to an HR-PIB storage tank 450. Thus, the fifth distillation effluent containing purified HR-PIB can leave the oligomer distillation unit 435 and can enter the HR-PIB storage tank 450 through a line 445. The HR-PIB storage tank 450 may include a plurality of HR-PIB storage tanks, e.g., 450A-450D where the HR-PIB storage tanks are segregated by molecular weight. The HR-PIB storage tanks 450 may be heated day tanks. Of note, each of the HR-PIB storage tanks 450A-450D can be, independently, a pipeline, a tank truck, a rail car, or another suitable means to transport the HR-PIB.

By utilizing one or more of such processes, the isobutylene conversion to HR-PIB can be 100% or nearly 100%.

When the novel feed integrated HR-PIB processing scheme is operated as above certain synergies can become evident namely, a total of 100% (or nearly 100%) of all butylenes, including all normal butylenes, in crude butylenes streams, can be converted to isobutylene. Oligomeric byproducts formed in the HR-PIB reactor of the HR-PIB processing unit can be recycled back to the C4 processing unit and through the processes described herein can be converted to isobutylene which can then be used as a feed for the HR-PIB processing unit, thereby rendering the isobutylene selectivity to HR-PIB of 100%, or nearly 100%, selectivity. Off-specification HR-PIB product can be recycled back to the oligomer cracking unit and cracked to isobutylene in the C4 processing unit which can then be used as feed to the HR-PIB processing unit. In addition, the unreacted isobutylene from the HR-PIB reactor of the HR-PIB processing unit can be recycled back to the C4 processing unit and can be converted back to a high purity isobutylene. This high purity isobutylene can be reused to feed the HR-PIB unit rendering the 100%, or nearly 100%, isobutylene conversion. Therefore, in some embodiments, the combination of 100%, or nearly 100%, conversion of all contained butylenes in crude butylenes streams to isobutylene, 100%, or nearly 100%, selectivity of isobutylene to product, 100%, or nearly 100%, isobutylene conversion in the HR-PIB reaction, and conversion of off-specification product to isobutylene means the yield of HR-PIB based on total butylenes in a crude butylenes feed stream can be 100%, or nearly 100%.

In addition, these inventive concepts can be applicable to other PIB processes, both existing and new HR-PIB plants, and Cosden technology plants.

Catalyst Complexes for Forming PIB

Catalysts for the polymerization processes to form PIB described herein can include Lewis acids, such as $BF_3$. The catalysts described herein are capable of forming PIB, such as HR-PIB. The catalyst complexes, like the Lewis acid catalysts, are capable of forming PIB and particularly HR-PIBs. Some of the catalyst complexes can include a Lewis acid (for example, $BF_3$) and a complexing agent.

In some embodiments, the Lewis acid catalyst can be complexed with a complexing agent. Alternatively, the Lewis acid catalyst can be used without a complexing agent. The catalyst systems can be solids, for example powders. The solid catalyst systems can be formed by contacting the Lewis acid catalyst alone (e.g., $BF_3$ gas) with a support material, or by complexing the Lewis acid catalyst complex (e.g., $BF_3$/complexing agent) with a support material.

Complexing agents can include linear, branched, cyclic, heterocyclic (for example, tetrahydrofuran and tetrahydropyran), aryl (such as phenol and benzyl alcohol), and heteroaryl compounds.

In some embodiments, the complexing agent can be a compound that has a lone pair of electrons (such as oxygen containing compounds and nitrogen containing compounds). Nitrogen containing compounds can include amines, polyamines (such as ethylene diamine), amides, polyamides, amino acids, polyamino acids, and polyaminocarboxylic acids such as ethylenediamine tetracetic acid (EDTA). In some embodiments, the nitrogen containing compound can be an unsubstituted $C_1$ to $C_{20}$ amine (such as alkylamines, including methyl amine, ethyl amine, propyl amine, decyl amine and lauryl amine), a substituted $C_1$ to $C_{20}$ amine, including alkanol amines (such as ethanol amine, diethanol amine, triethanol amine, propanol amine, diethylethanol amine), an unsubstituted $C_2$ to $C_{20}$ polyamine (such as diethylenetriamine, triethylenetetramine, tetraethylenepentamine, and heavy polyamine X (HPA X)), a substituted $C_2$ to $C_{20}$ polyamine, an unsubstituted $C_1$ to $C_{20}$ amide (such as formamide, acetamide, 2-propenamide, and benzamide), a substituted $C_1$ to $C_{20}$ amide (such as N,N-dimethylformamide (DMF), N,N-dimethypropanamide, N-methylacetamide, and N-phenylacetamide), aliphatic polyamides (such as Nylon 6 and Nylon 66), polyphthalamides (such as hexamethylenediamine terepthalate), aramids (such as Kevlar and Nomex), an amino acid (such as the 20 standard amino acids, for example aspartic acid and glycine), a polyamino acid (such as poly(hydroxypropyl-L-glutamine) and poly-L-leucine), polyaminocarboxylic acids.

Oxygen containing compounds (also known as oxygenates) that may be used include alcohols, ethers, ketones, aldehydes, and carboxylic acids. In some cases, the complexing agent can be an oxygen containing compound such as an alcohol or an ether (symmetrical or asymmetrical). In other cases, the complexing agent can be a $C_1$ to $C_{10}$ unsubstituted alcohol, a $C_1$ to $C_{10}$ substituted alcohol, a $C_2$ to $C_{20}$ unsubstituted ether, or a $C_2$ to $C_{20}$ substituted ether.

In some embodiments, the complexing agent can be an alcohol that lacks a beta hydrogen such as methanol, 2,2-dimethyl alcohols (for example, neopentyl alcohol, 2,2-dimethylbutanol, 2,2-dimethylpentanol, and 2,2-dimethylhexanol), benzyl alcohol, and ring-substituted benzyl alcohols.

In some embodiments, the complexing agent can contain more than one oxygen containing group per molecule, for example, glycols (substituted or unsubstituted) and polyols (substituted or unsubstituted), for example wherein each hydroxyl is in a primary position, or for example, a $C_1$ to $C_{10}$ glycol (substituted or unsubstituted) such as ethylene glycol, 1,4-butanediol, trimethylolethane (2-(hydroxymethyl)-2-methylpropane-1,3-diol; $C_5H_{12}O_3$), trimethylolpropane (2-(hydroxymethyl)-2-ethylpropane-1,3-diol; $C_6H_{14}O_3$), pentaerythritol (2,2-bis(hydroxymethyl)propane-1,3-diol; $C_5H_{12}O_4$), and tris(hydroxymethyl)aminomethane ($C_4H_{11}NO_3$).

In at least one embodiment, the complexing agent can be methanol, ethanol, isopropanol (also known as isopropyl alcohol), n-propanol (also known as propan-1-ol), neopentyl alcohol (also known as 2,2-dimethyl-1-propanol and neopentanol), dimethyl ether, diethyl ether, diisopropyl ether, diisobutyl ether, di-tert-butyl ether, methyl tert-butyl ether (MTBE), or ethylene glycol. In some embodiments, the oxygen containing compound can be methanol.

In some embodiments, the catalyst complex (e.g., the $BF_3$/complexing agent) can be formed by passing $BF_3$ gas through a pure anhydrous oxygen containing compound (or nitrogen containing compound) at a rate that allows the $BF_3$ to be efficiently absorbed.

In some embodiments, the mole ratio of complexing agent to $BF_3$ in the catalyst complex can be about 0.1 or more, such as from about 0.1 to about 10, such as from about 0.2 to about 5, such as from about 0.2 to about 2, such as from about 0.5 to about 2, such as from about 1.0 to about 1.9, such as from about 1.1 to about 1.3, such as about 1.2.

The catalyst system can include an unreactive support material. Suitable support materials for the catalyst and/or catalyst complex can include any support material that forms a stable adduct with $BF_3$. In at least one embodiment, the support material can be a porous support material comprising inorganic oxides. Other suitable support materials can include metal oxides doped with rare earth metals or rare earth metals themselves or a combination of both.

In some embodiments, the support material can be an inorganic oxide in a finely divided form, such as a powder. Suitable inorganic oxide materials for use in catalyst systems herein can include metal oxides of Group IIIA, Group IVA, and Group IVB of the Periodic Table of the Elements, such as alumina, silica, and titania, and a mixture thereof. Inorganic oxides may be employed either alone or in combination with the silica or alumina including titania and zirconia. Combinations of the support materials may be used, for example, silica-alumina, and silica-titania. In some embodiments, support materials can include $Al_2O_3$, $ZrO_2$, $TiO_2$, $SnO_2$, $CeO_2$, $SiO_2$, $SiO_2/Al_2O_3$, $Ce_2O_3$, $La_2O_3$, or a combination thereof. In some embodiments, support materials can include $SiO_2$, $Al_2O_3$, $SiO_2/Al_2O_3$, or a combination thereof. In at least one embodiment, the support material can be a rare earth metal oxide.

In at least one embodiment, the support material can have at least about 1% $Al_2O_3$ by weight, such as greater than about 3 wt %, such as greater than about 5 wt %, such as greater than about 10 wt %, greater than about 15 wt %, greater than about 20 wt %, greater than about 25 wt %, greater than about 30 wt %, greater than about 35 wt %, greater than about 40 wt %, greater than about 45 wt %, or greater than about 50 wt %, based on the total weight of the support material. Alternatively, the support material can have less than about 99 wt % $SiO_2$, such as less than about 97 wt %, such as less than about 95 wt %, such as less than about 90 wt %, less than about 85 wt %, less than about 80 wt %, less than about 75 wt %, less than about 70 wt %, less than about 65 wt %, less than about 60 wt %, less than about 55 wt %, or less than about 50 wt %, based on the total weight of the support material. Alternatively, the support material can have an $Al_2O_3$ of wt % ranges within those aforementioned weight percents.

In at least one embodiment, the support material can have at least about 1% $SiO_2$ by weight, such as greater than about 3 wt %, such as greater than about 5 wt %, greater than about 10 wt %, greater than about 15 wt %, greater than about 20 wt %, greater than about 25 wt %, greater than about 30 wt %, greater than about 35 wt %, greater than about 40 wt %, greater than about 45 wt %, or greater than about 50 wt %, based on the total weight of the support material. Alternatively, the support material can have less than about 99 wt % $SiO_2$, such as less than about 97 wt %, such as less than about 95 wt %, less than about 90 wt %, less than about 85 wt %, less than about 80 wt %, less than about 75 wt %, less than about 70 wt %, less than about 65 wt %, less than about 60 wt %, less than about 55 wt %, or less than about 50 wt %, based on the total weight of the support material. Alternatively, the support material can have a $SiO_2$ content of wt % ranges within those aforementioned weight percents.

In at least one embodiment, the support material can have a surface area greater than about 10 $m^2/g$, such as from about 10 $m^2/g$ to about 700 $m^2/g$, such as from about 50 $m^2/g$ to about 500 $m^2/g$, such as from about 100 $m^2/g$ and about 400 $m^2/g$. Alternatively, the surface area can be greater than about 150 $m^2/g$.

In at least one embodiment, the support material can have a pore volume greater than about 0.1 cc/g, such as from about 0.1 cc/g to about 4.0 cc/g, such as from about 0.5 cc/g to about 3.5 cc/g, such as from about 0.8 cc/g to about 3.0 cc/g.

In at least one embodiment, the support material can have a monodispersed particle size or a distribution of particle sizes with an average particle size greater than about 5 μm (for example, from about 5 μm to about 500 μm, such as from about 5 μm to about 200 μm, or from about 10 μm to about 100 μm).

In at least one embodiment, the support material can have an average pore size (diameter) greater than about 1 nm, such as from about 1 nm to about 100 nm, such as from about 5 nm to about 50 nm, such as from about 7.5 nm to about 35 nm. Alternatively, the pore size is greater than about 20 nm.

In at least one embodiment, the support material can have a pore volume greater than about 0.3 cc/g, such as greater than about 0.5 cc/g, such as greater than about 1.0 cc/g.

In at least one embodiment, the support material can have less than about 5 wt % $Fe_2O_3$, such as less than about 1 wt %, such as less than about 0.5 wt %, such as less than about 0.2 wt % based on the total weight of the support material.

In at least one embodiment, the support material can have less than about 5 wt % $Na_2O$, such as less than about 1 wt %, such as less than about 0.5 wt %, less than about 0.2 wt %, or less than about 0.02 wt % based on the total weight of the support material.

In at least one embodiment, the support material can have a high surface area, amorphous silica. For example, the support material can have a surface area of about 300 $m^2/g$ and a pore volume of about 1.65 $cm^3/gm$.

Other support materials can include the following: catalyst substrate spheres (CSS) 350™ gamma-alumina spheres (CSS350™ γ-$Al_2O_3$) which can be purchased from BASF Corporation; ALS 50™ $SiO_2/Al_2O_3$ (silica-alumina) support material which can be purchased from Pacific Industrial Development Corporation; and ALS75™ $SiO_2/Al_2O_3$ (silica-alumina) support material which can be purchased from Pacific Industrial Development Corporation. Table 2 shows the physical properties of these support materials prior to heating, calcining, and complexing with the catalyst and/or catalyst complexes.

TABLE 2

Physical Properties of Example Support Materials

| Property | CSS 350 Gamma-Alumina Spheres | ALS 50 Silica-Alumina | ALS 75 Silica-Alumina |
|---|---|---|---|
| $Al_2O_3$ (wt %) | 92.7 | 50.85 | 25.63 |
| Loss on Ignition (1000° C. for 1 h) (wt %) | 7.0 | 0.19 | 0.02 |
| $SiO_2$ (wt %) | 0.02 | 49.15 | 74.37 |
| $Fe_2O_3$ (wt %) | 0.02 | — | — |
| $Na_2O$ (wt %) | 0.2 | 0.01 | 0.01 |
| Sphere diameter (mm) | 3.2 | — | — |
| Particle Size: D10 (μm) | — | 12.25 | 11.13 |
| Particle Size: D50 (μm) | — | 39.05 | 38.63 |
| Particle Size: D90 (μm) | — | 79.01 | 79.53 |
| Packed Bulk Density (g/$cm^3$) | 0.769 | — | — |
| Loose Bulk Density (g/$cm^3$) | — | 0.38 | 0.28 |
| Surface Area ($m^2/g$) | 350 | 163.9 | 172.28 |
| Pore Volume (cc/g) | 0.50 | 1.06 | 1.45 |
| Pore Diameter (nm) | — | 25.79 | 33.48 |

The support material can be dry, that is, free (or essentially free) of absorbed water before addition of the catalyst or the catalyst complex. Drying of the support material can be effected by heating or calcining at a temperature of at least about 25° C., such as from about 100° C. to about 1000° C., such as from about 200° C. to 1000° C., such as from about 250° C. to 1000° C., such as from about 400° C. to about 900° C., such as from about 550° C. to about 700° C.; and for a time of from about 1 minute to about 100 hours, such as from about 1 minute to about 72 hours, such as from about 1 minute to about 60 hours, such as from about 2 hours to about 10 hours, such as about 2 hours, about 4 hours, 6 hours, or about 8 hours.

In some embodiments, the support material can be calcined when first manufactured and/or recalcined as received. The calcined support material can then be contacted with at least one of a mixture comprising $BF_3$ and a mixture comprising $BF_3$ and complexing agent.

Other support materials that can be used include organic supports that are a solid or that forms a solid when complexed with $BF_3$ and/or $BF_3$ and complexing agent. This organic support can be used instead of, or in combination with the inorganic oxide support material. In some embodiments, this support can be any solid organic complexing agent containing O or N functionality (or any functionality) that is capable of supporting $BF_3$ or $BF_3$ complexes. Alternatively, the support can be an organic complexing agent containing O or N functionality (or any functionality) that forms a solid when complexed $BF_3$ or $BF_3$ complexes. Examples of such complexing agents that act as supports include ion exchange resins such as anionic exchange resins and cationic exchanges resins, including strongly acidic cation exchange resins, weakly acidic cation exchange resins, strongly basic anionic exchange resins, and weakly basic anionic exchange resins. For example, Amberlyst™ and Amberlite™ resins (such as Amberlyst 15 sulfonic acid and Amberlite IRA 67 weak base (amine) resin) commercially available from Dow and Sigma Aldrich may be used as the support. The ion exchange resins may be used with or without calcining (or otherwise pretreated or heated). Dehydration (or otherwise heating) temperatures of the ion exchange resins include temperatures greater than about 25° C., such as from about 30° C. to about 200° C., such as from about 100° C. to about 200° C., such as about 150° C.; and for a time of from about 1 minute to about 100 hours, such as from about 1 minute to about 72 hours, such as from about 1 minute to about 60 hours, such as from about 2 hours to about 10 hours, such as about 2 hours, about 4 hours, 6 hours, or about 8 hours.

Catalyst Systems for Forming PIB

In some embodiments, the polymerization process can utilize a catalyst system. A catalyst system can be made from any catalyst described herein for the isobutylene polymerization, any support material described herein for the polymerization, any complexing agent described herein for the polymerization, and/or any catalyst complex described herein for the polymerization.

In some embodiments, the catalyst system can include $BF_3$ and a support material selected from the group consisting of $Al_2O_3$, $ZrO_2$, $TiO_2$, $SnO_2$, $CeO_2$, $SiO_2$, $SiO_2/Al_2O_3$, and a combination thereof, wherein the concentration of $BF_3$ can be greater than about 1% by weight, such as greater than about 5 wt %, such as greater than about 10 wt %, greater than about 20 wt %, greater than about 25 wt %, greater than about 30 wt %, greater than about 40 wt %, or greater than about 50 wt %, based on the total weight of the catalyst system (i.e., $BF_3$ plus the support material).

In some embodiments, the catalyst system can include $BF_3$ and an organic support material that is an ion exchange resin, e.g., an anionic exchange resin, a cationic exchange resin (such as Amberlyst™ and Amberlite™ resins), and/or a combination thereof, wherein the concentration of $BF_3$ can be greater than about 1% by weight, such as greater than about 5 wt %, such as greater than about 10 wt %, greater than about 20 wt %, greater than about 25 wt %, greater than about 30 wt %, such as about 40 wt %, based on the total weight of the catalyst system (i.e., $BF_3$ plus the support material).

In at least one embodiment, the catalyst system can include a combination of an inorganic oxide (e.g., $Al_2O_3$, $ZrO_2$, $TiO_2$, $SnO_2$, $CeO_2$, $SiO_2$, $SiO_2/Al_2O_3$, and a combination thereof) and an organic support (i.e., ion exchange resins, such as anionic and cationic exchange resins, for example Amberlyst™ and Amberlite™ resins).

In at least one embodiment, the catalyst system can further include a complexing agent, wherein the concentration of $BF_3$ is greater than about 1% by weight, such as greater than about 5 wt %, such as greater than about 10 wt %, greater than about 20 wt %, greater than about 25 wt %, greater than about 30 wt %, greater than about 40 wt %, or greater than about 50 wt %, based on the total weight of the catalyst system (i.e., $BF_3$ plus the complexing agent plus the support material). The actual concentration of F or B in the catalyst complex/support material depends on the complexing agent used.

In embodiments where the catalyst system is formed by adding to the support material a mixture comprising $BF_3$ and a complexing agent, the mole ratio of complexing agent to $BF_3$ can be about 0.1 or more, such as from about 0.1 to about 10, such as from about 0.2 to about 5, such as from about 0.2 to about 2, such as from about 0.5 to about 2, such as from about 1.0 to about 1.9, such as from about 1.1 to about 1.3, such as about 1.2.

In some embodiments, the weight ratio of support material to catalyst complex can be less than about 1:1, for example, less than about 0.5:1, or less than about 0.25:1.

In at least one embodiment, the catalyst composition can be about 65 wt % (based on the total weight of the catalyst system) of a $BF_3$-MeOH complex (about 1:1) on a $SiO_2/Al_2O_3$ support containing about 50 wt % $Al_2O_3$. In at least one embodiment, the catalyst composition can about 65 wt % (based on the total weight of the catalyst system) of a $BF_3$-MeOH complex (about 1:1) on an Amberlyst or Amberlite support.

In some embodiments, the catalyst system can be made by calcining (or otherwise heating) a metal oxide support material at a predetermined temperature for a predetermined time. Alternatively, the support material can be calcined (or otherwise heated) when first manufactured and/or recalcined (or reheated) as received. To the support material can be added (a) a mixture comprising a Lewis acid (for example, $BF_3$), (b) a mixture comprising a Lewis acid (for example, $BF_3$) and a complexing agent, or (c) both. The complexing agent may be a complexing agent described herein, and may be used in excess. The catalyst system obtained can be a solid.

In some embodiments, the catalyst system can be made by dehydrating (or otherwise heating) an ion exchange resin support material at a predetermined temperature for a predetermined time at operation 160 as described above. Alternatively, the support material can be dehydrated (or otherwise heated) when first manufactured and/or re-dehydrated (or reheated) as received. To the support material can be added (a) a mixture comprising a Lewis acid (for example, $BF_3$), (b) a mixture comprising a Lewis acid (for example, $BF_3$) and a complexing agent, or (c) both. The complexing agent may be any complexing agent described herein, and may be used in excess. The catalyst system obtained can be a solid.

In some embodiments, addition of the mixture comprising a Lewis acid can include adding $BF_3$ gas uncomplexed with any complexing agent (as described herein). In such embodiments, the support material may be contacted with excess $BF_3$ gas in a stainless steel cylinder at a pressure of greater than about 0 psig (0 kPa), such as from about 35 psig (about 250 kPa) to about 500 psig (about 3500 kPa), for about 4 hours. The cylinder can then be vented and excess $BF_3$ can be vented through a caustic scrubber.

Alternatively, the catalyst complex (e.g., the Lewis acid and complexing agent) can be added to the support material. In such cases, addition of the mixture comprising a Lewis acid and a complexing agent can include preforming the $BF_3$/complexing agent (the catalyst complex).

In some cases, the support material can be slurried in a solvent during contact with the catalyst complex. Examples of solvents include non-coordinating, non-oxygenate, non-reactive solvents including non-polar or weakly polar solvents, such as alkanes (for example, isopentane, hexane, n-heptane, octane, nonane, decane, undecane, dodecane, tridecane, tetradecane, pentadecane, hexadecane, and higher alkanes), although a variety of other materials including cycloalkanes, such as cyclohexane. Alternatively, halogenated hydrocarbons can be used as a solvent, such as carbon tetrachloride (CC14) and 1,2-dichloroethane.

During addition of the catalyst complex to the support material, the temperature of the mixture of the catalyst complex and the support material can be maintained from about 0° C. to about 70° C., such as from about 10° C. to about 60° C., such as from about 10° C. to about 50° C., such as about room temperature. The reaction mixture can be stirred while maintaining the temperature. Contact time, which may be the same as, or may include, the stirring time, can be greater than about 0.1 hours, such as from about 0.5 hours to about 24 hours, such as from about 2 hours to about 16 hours, such as from about 4 hours to about 8 hours.

The solid catalyst systems can be prepared by any means in which the support materials can be contacted with $BF_3$ gas and/or $BF_3$ catalyst complexes while maintaining the complexing temperature with the support materials as described above. The complexing reaction can be exothermic, and the reaction of the catalyst and/or catalyst complex with the support material can be controlled to avoid loss of $BF_3$. Loss of $BF_3$ may occur by breaking of the $BF_3$ complex bonds with the substrate, liberating $BF_3$ gas which is then, at the higher temperatures, lost from the solid substrate. The catalyst and/or catalyst complex may be added by any mechanical means that allows sufficient mixing of the catalyst and/or catalyst complex with the support material. In at least one embodiment, the support material can be placed in a rotating double cone mixer and the catalyst complex can be added ratably such that the temperature can be controlled within a desired range, e.g., not exceeding 50° C.–60° C.

In at least one embodiment, a tube-in-shell heat exchanger in which the support material is packed in the tubes and the cooling media is maintained on the jacket can be used. In some embodiments, $BF_3$ gas and/or $BF_3$ catalyst complexes can be passed over the support material in the tubes until a maximum absorption, but less than excess, is obtained as evidenced by $BF_3$ or of the $BF_3$ catalyst complex exiting the tubes. If less than a maximum absorption is desired, the catalyst system can be back-blended with uncomplexed support material to the desired $BF_3$ concentration.

The catalyst systems can be further modified by contacting the solid catalyst system with suitable modifying agents, for example, the oxygen containing and nitrogen containing complexing agents described above. Such embodiments can allow for the catalytic properties of the catalyst system(s) to be adjusted, for example, with respect to formation of alpha-vinylidene olefin isomers.

In some embodiments, the modifying agents can be added to the catalyst during the catalyst manufacturing step. Alternatively, the modifying agents can be added to the feed during the polymerization step to further fine tune the catalyst properties such as selectivity to form HR-PIB. Thus, there are various methods of preparing the catalyst system. In some embodiments, $BF_3$ gas can be added to the support material. Alternatively, $BF_3$-complexing agent can be added to the support material. In other embodiments, $BF_3$ gas can be added to the support material and then complexing agent can be added to the support material. In some embodiments, $BF_3$-complexing agent can be added to the support material, and then modifying agents can be added to the support material. In other embodiments, $BF_3$ gas can be added to the support material, then complexing agent can be added to the support material, and a modifying agent can be additionally added to the isobutylene feed. In some embodiments, $BF_3$-complexing agent can be added to the support material, then modifying agents can be added to the support material, and a modifying agent can be additionally added to isobutylene feed.

For example, the solid $BF_3$ complex can be contacted with the modifying agent in a stirred or otherwise agitated vessel such as a rotating drum in which the modifying agent can be sprayed onto the solid $BF_3$ complex and subsequently absorbed. The temperature can be maintained at less than about 50° C. by controlling the spray rate, or by cooling (for example with internal cooling coils or with an external jacket or both). The pressure can be greater than about 0 psig, such as from about 35 psig to about 500 psig with pressure provided by a nitrogen pad. Once the prescribed amount of modifying agent has been added, the mixture can be mixed for about an additional 4 hours after which time the mixing vessel can be vented to atmospheric pressure and the thus formed catalyst discharged to storage containers. The containers can be padded with about 1 psig to about 5 psig of nitrogen. The amount of modifying agent can be greater than about 0.5:1 mole ratio of modifying agent to $BF_3$, such as a mole ratio from about 1:1 to about 2:1, such as from about 1.1:1 to about 1.4:1.

As noted previously, embodiments of the present disclosure include polymerization processes wherein isobutylene is introduced to a catalyst system to form a polymer composition. The polymer compositions can include PIB, such as HR-PIB. For the polymerizations, $BF_3$ does not need to be mixed with a complexing agent, as $BF_3$ on the support material can be capable of forming polymer compositions including PIB, such as HR-PIB. In some embodiments, the catalyst can be complexed with a complexing agent and can be capable of forming the same polymer compositions. Typically, use of a complexing agent can help produce PIB with a high content of alpha vinylidene olefin isomer. While not wishing to be bound by theory, it is believed that complexing $BF_3$ mediates some of the acidity of $BF_3$ and reduces the rate of isomerization of initially formed alpha vinylidene isomers to more internally located and less reactive isomers.

The polymerization process may be catalyzed by a catalyst system described above. The feedstock for the polymerization process is a feedstock containing isobutylene. The isobutylene can be introduced to the polymerization reactor, can contact the catalyst (e.g., catalyst system), and can form a polymer composition. Polymer compositions are described below. In some embodiments, forming the reaction mixture comprising the feedstock and the catalyst system can be flowed into the polymerization reactor and/or maintaining a temperature of the polymerization reactor at a predetermined temperature or range of temperatures, for example, such as from about −35° C. to about 100° C.

In some cases, the catalyst system can be provided to the polymerization reactor as a slurry. The slurry may include the catalyst system and one or more oligomeric byproducts and/or light polymers from a PIB polymerization itself (for example, $C_8$ to $C_{16}$ oligomers, such as $C_8$ and/or $C_{12}$ PIB, and PIB having a molecular weight from about 350 Da to about 500 Da). In some embodiments, the slurry optionally comprises a non-polar carrier solvent such as alkanes from octane through hexadecane and higher alkanes.

In some embodiments, suitable concentrations of the catalyst system in the polymerization reaction mixture (e.g., the mixture containing isobutylene and catalyst system) can be greater than about 500 ppm based on a total weight of the catalyst feed, wherein a $BF_3$ concentration in the reaction mixture is about 125 ppm based on the total weight of the catalyst feed. In at least one embodiment, the concentration of the catalyst system in the polymerization reaction mixture can be from about 500 ppm to about 10,000 ppm based on a total weight of the catalyst feed, and wherein a $BF_3$ concentration in the reaction mixture can be from about 125 ppm to about 2,500 ppm based on the total weight of the catalyst feed. Alternatively, the concentration of the catalyst system in the polymerization reaction mixture can be from about 1,000 ppm to about 5,000 ppm based on a total weight of the catalyst feed, and wherein a $BF_3$ concentration in the polymerization reaction mixture can be from about 250 ppm to about 1,250 ppm based on the total weight of the catalyst feed.

Furthermore, although known polymerization techniques may be employed, processes according to certain embodiments utilize particular conditions (e.g., temperature and pressure). Temperatures generally may include a temperature of from about −35° C. to about 100° C., such as from about 0° C. to about 70° C. ° C. Pressure may depend on the desired scale of the polymerization system. For example, in some polymerizations, pressure may generally be conducted at the autogenous pressure of the reaction mixture at the selected reaction temperature. In some embodiments, the pressure of the polymerization reactor can be greater than about 0 psig (about 0 kPa), such as from about 35 psig (about 250 kPa) to about 500 psig (about 3500 kPa), such as from about 35 psig (about 250 kPa) to about 500 psig (about 3500 kPa), such as from about 50 psig (about 350 kPa) to about 300 psig (about 2100 kPa), such as from about 35 psig (about 250 kPa) to about 100 psig (about 700 kPa). Reaction pressure can depend on the type of polymerization reactor used. For continuous stirred tank reactors (CSTR) in which cooling is provided by ebullient cooling, that is by partial volatilization of the reaction mixture, the volatilization temperature, and thus the reaction temperature, can be dependent on reactor pressure. Lower pressure provides lower temperatures, and for practical purposes, with the lower limit set by the boiling point of the reaction mixture at ambient pressure. In the case of butylenes, this is around about −5° C. to about −10° C. In cases requiring lower temperatures, other inerts can be added with lower boiling points, such as propane. In loop reactors or CSTR not using ebullient cooling, reaction pressure may not be an issue when the reaction mixture is maintained in the liquid phase. For PIB this is typically greater than about 0 psig (about 0 kPa), for example greater than about 35 psig (about 250 kPa). The run time of the polymerization reaction can be up to about 600 minutes, such as up to about 300 minutes, such as from about 1 minute to about 250 minutes, from about 1 minute to about 150 minutes, or from about 1 to about 120 minutes. In some embodiments, the run time of the polymerization reaction can be less than about 4 minutes, such as less than about 3 minutes, less than about 2 minutes, or less than about 1 minute.

Times and temperatures can be controlled such that no significant olefin isomerization occurs during polymerization and conversion and molecular weights are in desirable ranges. Reaction temperatures and pressures, and polymer precursor concentrations, can be selected to control for the Mn of the polymer composition. For example, higher temperatures typically can provide polymer compositions with lower Mn.

Temperature control in the polymerization reactor can be achieved by offsetting the heat of polymerization with reactor cooling by using reactor jackets or cooling coils to cool the contents of the reactor, auto refrigeration, pre-chilled feeds, vaporization of liquid medium (diluent, polymer precursors, or solvent) or combinations of all three. In the case of CSTR with ebullient cooling, the boiling mixture can be cooled with a chilled overhead condenser. For non-ebullient cooled CSTR, any suitable type of heat exchanger can be used to chill the reactor jacket using any suitable cooling media. In some embodiments, a fast reactor can be used. A fast reactor is one in which the reactor is the heat exchanger with the reaction taking place in the tubes with cooling on the shell. Any type of suitable cooling media can be used depending mainly on operating temperature range. Adiabatic reactors with pre-chilled feeds may also be used. In some embodiments, the reactor(s) can be operated in as much of an isothermal mode as possible. Non-isothermal reactor operation can result in broader molecular weight distributions. In series operation, the second reactor temperature can be higher than the first reactor temperature. In parallel reactor operation, the temperatures of the two reactors can be independent.

Suitable reactors for the polymerization can include batch, continuous stirred tank reactor (CSTR), plug flow, fluidized bed, immobilized bed, and fixed bed. More than one reactor may be operated in series or parallel. These reactors may have or may not have internal cooling or heating, and the feeds may or may not be refrigerated.

CSTR

In some embodiments, and for CSTR, the catalyst system can be slurried with one or more oligomeric byproducts and/or light polymers from PIB polymerization itself (for example, $C_8$ to $C_{16}$ oligomers, such as $C_8$ and/or $C_{12}$ PIB, and PIB having a molecular weight from about 350 Da to about 500 Da), at about a 10 wt % concentration. The catalyst system slurry can then be injected into the incoming feed stream. In some embodiments, the catalyst system slurry can be injected into the incoming feed stream at a point where the physical distance between the injection point in the feed line and the point at which the feed enters the reactor is at a minimum. In some embodiments, the injection point for the catalyst may be on the suction side of the feed pump to provide mixing. In some embodiments, the slurry can optionally include a non-polar carrier solvent such as alkanes from octane through hexadecane and higher alkanes. In some embodiments, the concentration of the catalyst system in the reaction mixture for CSTR can be from about 1,000 ppm to about 2,000 ppm based on a total weight of the catalyst feed, wherein a $BF_3$ concentration can be from about 250 ppm to about 500 ppm based on the total weight of the feed. Residence times can be on the order of less than about 600 minutes, such as about 120 minutes, such as less than about 60 minutes, or from about 30 minutes to about 60 minutes, and can be controlled by catalyst system concentration. Higher catalyst system concentrations can increase the reaction rate. The polymerization reaction can be highly exothermic and a limiting factor to reaction rate can be the ability to remove the heat of reaction.

In conventional plants that utilize CSTR, the reaction mixture comprising the catalyst system can be flowing upward in the reactor, through at least a first portion and a second portion. The first portion of the reactor can be relatively narrow to provide higher velocity and higher catalyst system mixing. The second portion of the reactor can be wider to provide lower velocity and less catalyst system mixing, allowing for some settling of the catalyst system back into the reaction zone. The crude reaction mixture can exit near the top of the reactor with some catalyst system being carried out with the exiting crude reaction mixture. The catalyst system exiting the reactor can be made up with the catalyst system injection such that a constant catalyst system amount is maintained in the reactor. The reaction temperature can be maintained by vaporization of a portion of the isobutylene containing feed controlled by the reactor pressure; higher reactor pressure can give higher reaction temperature according to the vapor pressure curve of the system butylenes. Mn of the polymer can be controlled by reaction temperature with higher reaction temperature giving lower Mn. Reaction temperatures from about −5° C. to about 5° C. can provide polymers having an Mn of about 2,300 daltons. Reaction temperatures from about 18° C. to about 22° C. can provide polymers having an Mn of about 1,000 daltons. The crude reaction mixture leaving the reactor can be treated with aqueous caustic streams to quench and wash out the catalyst system.

Alternatively, these plants can be modified to include a catalyst system filtration (or other solid-liquid separation devices as described below) to remove the catalyst system thereby eliminating the water washing operations and the need to dispose of waste water containing catalyst system residues. Optionally, a water washing operation may be performed depending on application or type of plant. Removal of the catalyst system also allows for recycling of the catalyst system. The plants can also include one or more distillation units as described below.

Tubular Loop Reactors

In some embodiments, and for fast reactor modes, the polymerization reactor can be a tube-in-shell heat exchanger with the reaction taking place in the tubes and cooling provided through the shell side of the heat exchanger with the heat of reaction taken out by an external chiller unit.

One reactor design can be a two-pass heat exchanger. Using a slurried catalyst system, the reaction can be carried out in the liquid phase at pressures of at least about autogenous pressures, typically greater than about 0 psig (0 kPa), such as from about 35 psig (about 250 kPa) to about 300 psig (about 2100 kPa), from about 50 psig (about 345 kPa) to about 300 psig (about 2100 kPa), or from about 100 psig (about 700 kPa) to about 150 psig (about 1000 kPa).

In some embodiments, a tubular loop reactor can be used. In such embodiments, the circulation loop can be provided to deliver high velocity in the tubes at a Reynold's number of the circulating liquid in the tubes greater than about 2,000. In some embodiments the residence time in the reactor can be less than about 120 minutes, such as less than about 90 minutes, less than about 60 minutes, less than about 30 minutes, less than about 10 minutes, less than about 4 minutes, less than about 3 minutes, less than about 2 minutes, or less than about 1 minute; Alternatively, the residence time in the reactor can be from about 30 seconds to about 4 minutes. Reynolds numbers greater than about 2,000 can allow for turbulent flow in the tubes which increases the heat exchange and the ability to remove the heat of reaction in very short periods of time. The ability to quickly remove the heat of reaction can allow for operation at very short residence times. The concentration of the catalyst system in the polymerization reaction mixture can be from about 500 ppm to about 10,000 ppm based on a total weight of the catalyst feed, and wherein a $BF_3$ concentration in the polymerization reaction mixture can be from about 125 ppm to about 2,500 ppm based on the total weight of the catalyst feed. In some embodiments, the concentration of the catalyst system in the polymerization reaction mixture can be from about 1,000 ppm to about 5,000 ppm based on a total weight of the catalyst feed, and wherein the $BF_3$ concentration in the polymerization reaction mixture can be from about 250 ppm to about 1,250 ppm based on the total weight of the catalyst feed. Alternatively, the concentration of the catalyst system in the polymerization reaction mixture can be greater than about 2,000 ppm based on a total weight of the catalyst feed, and wherein the $BF_3$ concentration can be greater than about 500 ppm based on the total weight of the catalyst feed.

In some embodiments, the reactor system can be a tubular loop reactor in which the Reynold's number of the circulating liquid in the tubes can be greater than about 2,000 and the residence time in the reactor can be less than about 120 minutes, such as less than about 90 minutes, less than about 60 minutes, less than about 30 minutes, less than about 10 minutes, less than about 4 minutes, less than about 3 minutes, less than about 2 minutes, or less than about 1 minute, or alternatively from about 30 seconds to about 4 minutes, such that the solid catalyst system is immobilized in the tubes by attaching the catalyst system particles to a suitable substrate. Because the catalyst system can be constrained in the tubes, no post reaction recovery is required. Suitable substrate compositions and geometries for attaching the solid $BF_3$ catalyst system particles can include ceramic mats such as those sold by NGK Insulators for use in modern catalytic convertors, or wire mesh or wire fibers. As such, the catalyst system particles (or catalyst complex) can be used in fixed bed reactors to produce HR-PIB. The solid catalyst systems of the present disclosure can be further attached or otherwise immobilized to other solid substrates chemically, physically, or mechanically means, or a combination thereof.

For tubular loop reactors, the catalyst system can be slurried with one or more oligomeric byproducts and/or light polymers from PIB polymerization itself (for example, $C_8$ to $C_{16}$ oligomers, such as $C_8$ and/or $C_{12}$ PIB, and PIB having a molecular weight from about 350 Da to about 500 Da), at about 10 wt % catalyst system concentration. The catalyst system slurry can then be injected into the incoming feed stream. In some embodiments, the catalyst system slurry can be injected into the incoming feed stream at a point where the physical distance between the injection point in the feed line and the point at which the feed enters the reactor is at a minimum. In some embodiments, the injection point for the catalyst may be on the suction side of the feed pump to provide mixing. In some embodiments, the slurry optionally includes a non-polar carrier solvent such as alkanes from octane through hexadecane and higher alkanes.

Each of the various polymerization processes to form PIB, e.g., HR-PIB described herein can be carried out using general polymerization techniques known in the art. Any suitable suspension, homogeneous, bulk, slurry, solution slurry, or gas phase polymerization process known in the art can be used. Such processes can be run in a batch, semi-batch, or continuous mode. In some embodiments, homogeneous polymerization processes and slurry processes are used. Alternatively, no solvent or diluent can be present or added in the reaction medium, (except for the small amounts used as the carrier for the catalyst system or other additives, or amounts typically found with the polymer precursors). In another embodiment, the process can be a slurry process. In the slurry process, a suspension of supported catalyst can be employed and polymer precursors can be polymerized on the catalyst particles and/or catalyst systems.

In some slurry process embodiments, the suspension can include diluent. The suspension can be intermittently or continuously removed from the reactor where the volatile components are separated from the polymer and recycled, optionally after a distillation, to the reactor.

In some embodiments, the polymerization can be conducted in an aliphatic hydrocarbon solvent, e.g., isobutane, butane, pentane, isopentane, hexanes, isohexane, heptane, octane, dodecane, and a mixture thereof, and the like. Other additives may also be used in the polymerization, as desired, such as one or more scavengers, promoters, modifiers, reducing agents, and oxidizing agents.

PIB Polymer Compositions

The polymerization processes described herein can produce polymer compositions, such as PIB, e.g., HR-PIB.

In at least one embodiment, the polyisobutylene can have a number average molecular weight, Mn, of about 320 daltons or more, such as from about 320 daltons to about 10,000 daltons, such as from about 350 daltons to about 5,000 daltons, or from about 700 daltons to about 2,250 daltons. In at least one embodiment, the polyisobutylene can have an Mn of about 350 daltons, about 700 daltons, about 950 daltons, about 1300 daltons, or about 2,250 daltons.

In at least one embodiment, the polyisobutylene can include a first portion comprising polymer chains having alpha vinylidene groups, and one or more of a second portion comprising polymer chains having beta vinylidene groups and a third portion comprising polymer chains having internal vinylidene groups, wherein: the first portion can be greater than about 75 wt %, such as greater than about 80 wt %, such as greater than about 82 wt %, greater than about 85 wt %, greater than about 87 wt %, greater than about 90 wt %, greater than about 92 wt %, greater than about 94 wt %, or greater than about 95 wt % based on a total weight of the composition, and a total content of the second portion plus the third portion can be less than about 25 wt %, such as less than about 20 wt %, less than about 18 wt %, less than about 15 wt %, less than about 13 wt %, less than about 10 wt %, less than about 8 wt %, less than about 6 wt %, or less than about 5 wt % based on the total weight of the composition.

In at least one embodiment, the polyisobutylene can have a polydispersity index (PDI), which is the ratio of Mw/Mn, of about 5 or less, such as about 2.5 or less, about 2 or less, about 1.5 or less, or about 1.3 or less.

Embodiments Listing

The present disclosure provides, among others, the following embodiments, each of which may be considered as optionally including any alternate embodiments.

A1. A process to convert a feed comprising: introducing a feed comprising isobutylene to an oligomerization catalyst in an oligomerization reactor to form a first reactor effluent comprising one or more oligomers of isobutylene; introducing the first reactor effluent to a first distillation unit to form a first distillation effluent and a second distillation effluent, the second distillation effluent comprising one or more oligomers of isobutylene; and introducing the second distillation effluent to a cracking reactor to form a cracking reactor effluent, the cracking reactor effluent comprising a high purity isobutylene.

A2. The process of paragraph A1, further comprising introducing the first distillation effluent to an isomerization reactor to form an isomerized product effluent, the isomerized product effluent enriched in isobutylene; combining the isomerized product effluent with the feed comprising isobutylene; and introducing the isomerized product effluent to the oligomerization reactor.

A3. The process of paragraph 2, further comprising purging butadiene, and optionally other inert butanes, from the isomerized product effluent.

A4. The process of any of paragraphs A1-A3, further comprising: introducing the second distillation effluent to a second distillation unit prior to the cracking reactor to form a third distillation effluent; and introducing the third distillation effluent to the cracking reactor.

A5. The process of paragraph A4, wherein the introducing the second distillation effluent to a second distillation unit prior to the cracking reactor forms a fourth distillation effluent, the fourth distillation effluent comprising diisobutylene.

A6. The process of any of paragraphs A1-A5, further comprising introducing the cracking reactor effluent to a polishing column to form a first polishing column effluent and a second polishing column effluent, the first polishing column effluent comprising the high purity isobutylene.

A7. The process of paragraph A6, further comprising: combining the second polishing column effluent with the feed comprising isobutylene; and introducing the second polishing column effluent to the oligomerization reactor.

A8. The process of any of paragraphs A1-A7, further comprising introducing the cracking reactor effluent, the first polishing column effluent, or a combination thereof to a polymerization reactor to form a polymerization reactor effluent comprising a high reactive polyisobutylene.

A9. The process of paragraph A8, further comprising introducing the polymerization reactor effluent to a debutanizer column to form a first debutanized effluent and a second debutanized effluent, the first debutanized effluent comprising the high reactive polyisobutylene and optionally oligomer byproducts, and the second debutanized effluent comprising the high purity isobutylene.

A10. The process of paragraph A9, further comprising introducing the first debutanized effluent to a third distillation unit to form a fifth distillation effluent and a sixth distillation effluent, the fifth distillation effluent comprising the high reactive polyisobutylene and the sixth distillation effluent comprising the oligomer byproducts.

A11. The process of paragraph A10, further comprising combining the sixth distillation effluent with the second distillation effluent, the third distillation effluent, or a combination thereof; and introducing the sixth distillation effluent to the cracking reactor.

A12. The process of paragraph A9, further comprising: combining the second debutanized effluent with the cracking reactor effluent; and introducing the second debutanized effluent to the polishing column.

A13. The process of any of paragraphs A1-A12, wherein the feed comprising isobutylene comprises a feedstock containing normal butylenes.

A14. The process of any of paragraphs A1-A12, wherein the feed comprising isobutylene comprises a byproduct from an olefin plant, raffinate-1, raffinate-2, or a combination thereof.

A15. The process of any of paragraphs A1-A14, wherein a conversion of the feed comprising isobutylene to a high purity isobutylene is about 80% or greater, based on a total butylene content in the feed.

A16. The process of any of paragraphs A8-A15, wherein a conversion of the feed comprising isobutylene to a high reactive polyisobutylene is about 80% or greater, based on a total butylene content in the feed.

A17. The process of any of paragraphs A1-A16, wherein the feed comprising isobutylene has an isobutylene content of 10 wt % or less, based on the total weight of the feed.

B1. A process to convert a feed comprising: introducing a feed comprising isobutylene to an oligomerization catalyst in an oligomerization reactor to form a first reactor effluent comprising one or more oligomers of isobutylene; introducing the first reactor effluent to a first distillation unit to form a first distillation effluent and a second distillation effluent, the second distillation effluent comprising one or more oligomers of isobutylene; introducing the second distillation effluent to a cracking reactor to form a cracking reactor effluent, the cracking reactor effluent comprising a high purity isobutylene; introducing the first distillation effluent to an isomerization reactor to form an isomerized product effluent, the isomerized product effluent enriched in isobutylene; combining the isomerized product effluent with the feed comprising isobutylene; and introducing the isomerized product effluent to the oligomerization reactor.

B2. The process of paragraph B1, further comprising introducing the cracking reactor effluent to a polishing column to form a first polishing column effluent and a second polishing column effluent, the first polishing column effluent comprising the high purity isobutylene.

B3. The process of paragraphs B1 or B2, further comprising introducing the cracking reactor effluent, the first polishing column effluent, or a combination thereof to a polymerization reactor to form a polymerization reactor effluent comprising a high reactive polyisobutylene.

B4. The process of any of paragraphs B1-B3, further comprising: introducing the second distillation effluent to a second distillation unit prior to the cracking reactor to form a third distillation effluent; and introducing the third distillation effluent to the cracking reactor.

B5. The process of paragraph B4, wherein the introducing the second distillation effluent to a second distillation unit prior to the cracking reactor forms a fourth distillation effluent, the fourth distillation effluent comprising diisobutylene.

B6. The process of paragraph B5, further comprising: combining the second polishing column effluent with the feed comprising isobutylene; and introducing the second polishing column effluent to the oligomerization reactor.

B7. The process of any of paragraphs B3-B6, further comprising introducing the polymerization reactor effluent to a debutanizer column to form a first debutanized effluent and a second debutanized effluent, the first debutanized effluent comprising the high reactive polyisobutylene and optionally oligomer byproducts, and the second debutanized effluent comprising the high purity isobutylene.

B8. The process of paragraph B7, further comprising introducing the first debutanized effluent to a third distillation unit to form a fifth distillation effluent and a sixth distillation effluent, the fifth distillation effluent comprising the high reactive polyisobutylene and the sixth distillation effluent comprising the oligomer byproducts.

B9. The process of paragraph B8, further comprising combining the sixth distillation effluent with the second distillation effluent, the third distillation effluent, or a combination thereof; and introducing the sixth distillation effluent to the cracking reactor.

B10. The process of paragraph B7, further comprising combining the second debutanized effluent with the cracking reactor effluent; and introducing the second debutanized effluent to the polishing column.

B11. The process of any of paragraphs B1-B10, wherein the feed comprising isobutylene comprises a feedstock containing normal butylenes.

B12. The process of any of paragraphs B1-B10, wherein the feed comprising isobutylene comprises a byproduct from an olefin plant, raffinate-1, raffinate-2, or a combination thereof.

B13. The process of any of paragraphs B1-B12, wherein a conversion of the feed comprising isobutylene to a high purity isobutylene is about 80% or greater, based on a total butylene content in the feed.

B14. The process of any of paragraphs B3-13, wherein a conversion of the feed comprising isobutylene to a high reactive polyisobutylene is about 80% or greater, based on a total butylene content in the feed.

B15. The process of any of paragraphs B1-14, further comprising purging butadiene from the isomerized product effluent.

C1. An apparatus comprising: a feed line coupled to a first end of an oligomerization reactor; a first distillation unit coupled with a second end of the oligomerization reactor; a first end of a cracking reactor coupled to a second end of the first distillation unit via a first line; an isomerization reactor coupled to: a third end of the first distillation unit at a first end of the isomerization reactor; and the feed line.

C2. The apparatus of paragraph C1, further comprising a polishing column coupled to a second end of the cracking reactor at a first end of the polishing column via a second line.

C3. The apparatus of paragraph C2, further comprising a polymerization reactor coupled to a second end of the polishing column at a first end of the polymerization reactor.

C4. The apparatus of paragraph C3, further comprising a debutanizer column coupled to: a second end of the polymerization reactor at a first end of the debutanizer column; a first end of a second distillation unit at a second end of the debutanizer column; and optionally, the second line at a third end of the debutanizer column.

C5. The apparatus of paragraph C4, further comprising a HR-PIB storage tank coupled to a second end of the second distillation unit.

C6. The apparatus of any of paragraphs C5, wherein a third end of the second distillation unit is coupled to the first line C7. The apparatus of any of paragraphs C1-C6, further comprising an optional third distillation unit located at a point along the first line.

C8. The apparatus of paragraph C7, further comprising a diisobutylene storage tank coupled to a third end of the third distillation unit.

C9. The apparatus of any of paragraphs C4-C8, wherein a third end of the second distillation unit is coupled to the first line.

C10. The apparatus of any of paragraphs C2-C9, wherein a third end of the polishing column is coupled to the feed line.

C11. The apparatus of any of paragraphs C2-C10, further comprising a high purity isobutylene storage tank coupled to a fourth end of the polishing column at a first end of the high purity isobutylene storage tank.

C12. The apparatus of paragraph C11, wherein a second end of the high purity isobutylene storage tank is coupled to a third end of the polymerization reactor.

C13. The apparatus of any of paragraphs C1-C12, further comprising a butadiene storage tank, a pipeline, a tank truck, a rail car, and/or other suitable means to transport the butadiene purge to a butadiene processing facility.

D1. A process for converting a crude C4 feedstock, comprising: introducing a crude C4 feedstock to a C4 processing unit, and forming a product mixture, the product mixture comprising an isobutylene.

D2. The process of paragraph D1, wherein the crude C4 feedstock comprises a byproduct from an olefin plant, raffinate-1, raffinate-2, or a combination thereof.

D3. The process of paragraph D1 or paragraph D2, wherein a conversion of the crude C4 feedstock to a high purity isobutylene is about 80% or greater, based on a total butylene content in the crude C4 feedstock.

D4. The process of any of paragraphs D1-D3, wherein the conversion of the crude C4 feedstock to the isobutylene is 95% or greater, based on the total butylene content in the crude C4 feedstock.

D5. The process of any of paragraphs D1-D4, wherein the processing unit comprises a plurality of unit operations, the plurality of unit operations being operated such that isobutylene is the predominate product.

D6. The process of any of paragraphs D1-D5, wherein the plurality of unit operations comprises one or more of: performing an isobutylene oligomerization, performing an oligomer back-cracking, performing an olefin skeletal isomerization, and performing a butadiene concentration.

D7. The process of paragraphs D1-D6, the crude C4 feedstock comprises isobutylene, and optionally normal butylenes, further comprising: reacting the isobutylene in an isobutylene oligomerization reactor to form dimers and higher oligomers of isobutylene.

D8. The process of paragraph D7, wherein the isobutylene reacts selectively.

D9. The process of paragraphs D7 or D8, further comprising reacting an amount of unreacted normal butylenes in a skeletal isomerization reactor to form an equilibrium ratio of isomeric butylenes, the isomeric butylenes comprising isobutylene.

D10. The process of paragraph D9, wherein the skeletal isomerization reactor is operated under conditions such that an amount of isobutylene formed is maximized.

D11. The process of paragraphs D9 or D10, further comprising directing an effluent from the skeletal isomerization reactor to the isobutylene oligomerization reactor.

D12. The process of any of paragraphs D7-D11, further comprising cracking the dimers and higher oligomers in an oligomer cracking unit to form a cracking unit product comprising yielding essentially pure isobutylene.

D13. The process of paragraph D12, wherein the cracking unit product consists essentially of isobutylene.

D14. The process of any of paragraphs D1-D13, wherein the processing unit comprises a butadiene concentration unit, the butadiene concentration unit being a purge stream operated such that the butadiene contained in the crude C4 feedstock is concentrated to a commercially viable amount.

D15. The process of any of paragraphs D1-D14 in which the C4 processing unit is integrated with an olefin plant and is operated at a site where the crude C4 feedstock is formed.

D16. The process of any of paragraphs D1-D15, wherein the crude C4 feedstock has an isobutylene content of 10 wt % or less, based on the total weight of the feed.

E1. A process of producing a high reactive polyisobutylene (HR-PIB) in a HR-PIB processing unit comprising: introducing an isobutylene containing feed to a HR-PIB polymerization catalyst in a HR-PIB reactor; and forming a HR-PIB in the HR-PIB reactor.

E2. The process of paragraph E1, wherein the HR-PIB processing unit is integrated with the C4 processing unit of any of paragraphs D1-D16.

E3. The process of paragraph E1 or paragraph E2, wherein the HR-PIB processing unit uses the isobutylene effluent from the C4 processing unit as a feed to the HR-PIB reactor.

E4. The process of any of paragraphs E1-E3, further comprising directing an effluent comprising dimers and oligomeric byproducts formed in the HR-PIB reactor to a cracking operation of a C4 processing unit.

E5. The process of any of paragraphs E1-E4, wherein a conversion of the feed comprising isobutylene to a high reactive polyisobutylene is about 80% or greater, based on a total butylene content in the feed.

E6. The process of paragraph E5, wherein the conversion is essentially about 100%.

E7. The process of any of paragraphs E1-E6, wherein the HR-PIB reactor is a fast reactor.

E8. The process of any of paragraphs E1-E7, wherein the HR-PIB polymerization catalyst is a solid dispersible catalyst.

E9. The process of any of paragraphs E1-E8, wherein the isobutylene containing feed comprises a crude C4 feed from an olefin plant steam cracker.

E10. The process of any of paragraphs E1-E9, wherein the isobutylene containing feed comprises raffinate-1, raffinate-2, or a combination thereof.

E11. The process of any of paragraphs E1-E10, wherein the HR-PIB polymerization catalyst comprises a solid dispersible $BF_3$ complex catalyst.

E12. The process of any of claims E1-E11, wherein a residence of the isobutylene containing feed in the HR-PIB reactor is about 4 minutes or less.

A17. The process of any of paragraphs E1-E12, wherein the isobutylene containing feed has an isobutylene content of 10 wt % or less, based on the total weight of the feed.

G1. A process of producing polyisobutylene, other than a HR-PIB process, comprising: forming polyisobutylene in a polyisobutylene reactor.

G2. The process of claim G1, wherein the process of producing polyisobutylene is an existing Cosden process.

G3. The process of claim G2, wherein the Cosden process is retrofitted to use a solid $BF_3$ complex catalyst, rendering the Cosden process capable of making HR-PIB.

G4. The process of claim G3, wherein the process is free of an $AlCl_3$ catalyst.

G5. The process of claim G2 or claim G4, wherein the process is retrofitted with a fast-reactor.

G6. The process of any of claims G1-G5, wherein the process is free of a continuous stirred tank reactor (CSTR).

G7. The process of any of claims G1-G6, wherein a conversion of the isobutylene containing feed to a polyisobutylene is about 80% or greater, based on a total butylene content in the isobutylene containing feed.

G8. The process of claim G7, wherein the conversion is essentially about 100%.

H1. A process to produce diisobutylene, comprising: introducing an isobutylene containing feed to a HR-PIB polymerization catalyst in a HR-PIB processing unit, the HR-PIB processing unit comprising an HR-PIB reactor; and forming diisobutylene in the HR-PIB reactor.

H2. The process of paragraph H1, wherein the DIB is an overhead stream of an isobutylene oligomerization reactor, such as the isobutylene reactor of paragraph D7.

H3. The process of paragraph H1 or paragraph H2, wherein an amount of DIB formed is about 75% or greater.

H4. The process of any of paragraphs H1-H3, wherein a sulfur content of DIB is about 50 ppm or less.

I1. A process to produce diisobutylene (DIB) in a DIB processing unit, wherein the DIB processing unit is integrated with a C4 processing unit and a HR-PIB processing unit.

The present disclosure provides a novel processing scheme to convert the normal butylenes (e.g., 1-butene and 2-butenes) in crude C4 streams to a product containing isobutylene and minimal amounts of the normal butylenes. Such a process can provide for an economically efficient production of isobutylene. Moreover, the present disclosure includes using that isobutylene formed to make polyisobutylene ("PIB") and high reactive polyisobutylene ("HR-PIB"). Furthermore, the present disclosure includes processes for the C4 conversion at the olefin plant instead of sending the C4 streams to an off-site processing facility.

Conventional methods of making isobutylene utilize alcohols (e.g., methanol) to convert raffinate streams to ethers (e.g., MTBE) and a subsequent back-cracking of the ether to make isobutylene and alcohol. These conventional methods suffer from using and producing alcohols and oxygenates in the process. Alcohols and oxygenates are detrimental impurities in isobutylene, particularly when the isobutylene is used to produce polyisobutylene. In contrast, the process described herein advantageously avoids the use of alcohols. This is a technological and economical improvement over conventional processes. The processes described herein is more cost-efficient and cleaner, and can convert all, or nearly all, of the normal butylenes in a C4 containing feedstock to isobutylenes with high purity. Conventional methods cannot do this. In contrast to conventional methods, the processes described herein can also convert all, or nearly all, of the normal butylenes in a C4 containing feedstock to polyisobutylene and HR-PIB.

In addition, the oligomer cracking unit to produce isobutylene is an improvement over conventional tert-ether cracking in that there is no alcohol byproduct that could be a contaminant in the isobutylene product and would require additional purification, especially since alcohols are oxygenates which are PIB catalyst poisons. Also, the oligomer cracking unit, when integrated with a HR-PIB unit, can be used to crack byproduct oligomers and any off-specification HR-PIB product to isobutylene. The process can also allow for a high value use of the low-value normal butylenes and nearly 100% selectivity of isobutylene to HR-PIB.

Typically, feedstocks for HR-PIB processes are isobutylene containing streams which do not contain normal butylenes, such as high purity isobutylene containing 99+% isobutylene, isobutylene concentrate (IBC) containing 85-95% isobutylene with the balance being isobutane, dehydro effluent (DHE) containing 45-50% isobutylene with the balance being isobutane, and/or combinations of these streams with the corresponding intermediate isobutylene concentrations. These streams, however, are not available in many parts of the world, thereby limiting the areas in which HR-PIB processes can be operated and limiting the commercial usefulness of the HR-PIB processes worldwide. In these and other areas, only CC4 and raffinate streams are available, and as discussed above, these streams contain low concentrations of isobutylene with the normal butylenes being the major components. The reaction of normal butylenes in the conventional HR-PIB process reduces the alpha vinylidene olefin isomer content such that the PIB produced is not true HR-PIB. Even if the conventional processes could be operated such that the normal butylenes do not react, the yield of HR-PIB based on the total feed stream is low. The current disclosure solves, at least, this problem.

The phrases, unless otherwise specified, "consists essentially of" and "consisting essentially of" do not exclude the presence of other steps, elements, or materials, whether or not, specifically mentioned in this specification, so long as such steps, elements, or materials, do not affect the basic and novel characteristics of this disclosure, additionally, they do not exclude impurities and variances normally associated with the elements and materials used.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, within a range includes every point or individual value between its end points even though not explicitly recited. Thus, every point or individual value may serve as its own lower or upper limit combined with any other point or individual value or any other lower or upper limit, to recite a range not explicitly recited.

All documents described herein are incorporated by reference herein, including any priority documents and/or testing procedures to the extent they are not inconsistent with this text. As is apparent from the foregoing general description and the specific embodiments, while forms of this disclosure have been illustrated and described, various modifications can be made without departing from the spirit and scope of this disclosure. Accordingly, it is not intended that this disclosure be limited thereby. Likewise, the term "comprising" is considered synonymous with the term "including" for purposes of United States law. Likewise whenever a composition, an element or a group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

While this disclosure has been described with respect to a number of embodiments and examples, those skilled in the art, having benefit of this disclosure, will appreciate that other embodiments can be devised which do not depart from the scope and spirit of this disclosure.

I claim:

1. A process to convert a feed, comprising:
   introducing a feed comprising isobutylene to an oligomerization catalyst in an oligomerization reactor to form a first reactor effluent comprising one or more oligomers of isobutylene;
   introducing the first reactor effluent to a first distillation unit to form a first distillation effluent and a second distillation effluent, the second distillation effluent comprising the one or more oligomers of isobutylene;
   introducing the second distillation effluent to a cracking reactor to form a cracking reactor effluent, the cracking reactor effluent comprising a high purity isobutylene;
   introducing the cracking reactor effluent to a polishing column to form a first polishing column effluent and a second polishing column effluent, the first polishing column effluent comprising the high purity isobutylene;
   combining the second polishing column effluent with the feed comprising isobutylene; and
   introducing the second polishing column effluent and the feed comprising isobutylene to the oligomerization reactor.

2. The process of claim 1, further comprising:
   introducing the first distillation effluent to an isomerization reactor to form an isomerized product effluent, the isomerized product effluent enriched in isobutylene; and
   introducing the isomerized product effluent to the oligomerization reactor.

3. The process of claim 2, further comprising purging butadiene from the isomerized product effluent.

4. The process of claim 2, further comprising combining the isomerized product effluent enriched in isobutylene with the feed comprising isobutylene before introducing the isomerized product effluent to the oligomerization reactor.

5. The process of claim 1, further comprising:
   introducing the second distillation effluent to a second distillation unit prior to the cracking reactor to form a third distillation effluent; and introducing the third distillation effluent to the cracking reactor.

6. The process of claim 5, wherein the introducing the second distillation effluent to a second distillation unit prior to the cracking reactor forms a fourth distillation effluent, the fourth distillation effluent comprising diisobutylene.

7. The process of claim 1, further comprising introducing the cracking reactor effluent, the first polishing column effluent, or a combination thereof to a polymerization reactor to form a polymerization reactor effluent comprising a high reactive polyisobutylene.

8. The process of claim 7, further comprising introducing the polymerization reactor effluent to a debutanizer column to form a first debutanized effluent and a second debutanized effluent, the first debutanized effluent comprising the high reactive polyisobutylene, and the second debutanized effluent comprising the high purity isobutylene.

9. The process of claim 8, further comprising introducing the first debutanized effluent to a third distillation unit to form a fifth distillation effluent and a sixth distillation effluent, the fifth distillation effluent comprising the high reactive polyisobutylene.

10. The process of claim 9, further comprising combining the sixth distillation effluent with the second distillation effluent; and introducing the sixth distillation effluent to the cracking reactor.

11. The process of claim 8, further comprising introducing the second debutanized effluent to the polishing column.

12. The process of claim 8, further comprising combining the second debutanized effluent with the cracking reactor effluent prior to introducing the second debutanized effluent to the polishing column.

13. The process of claim 1, wherein a conversion of the feed comprising isobutylene to the high purity isobutylene is about 80% or greater, based on a total butylene content in the feed.

14. The process of claim 13, wherein the conversion of the feed comprising isobutylene to the high purity isobutylene is about 90% or greater based on the total butylene content in the feed.

15. The process of claim 1, wherein the feed is raffinate-1.

16. The process of claim 1, wherein the oligomerization catalyst comprises $BF_3$ and a support material.

17. The process of claim 16, wherein a concentration of $BF_3$ in the oligomerization catalyst is greater than 30 wt %.

18. The process of claim 16, wherein the support material comprises $Al_2O_3$, $ZrO_2$, $TiO_2$, $SnO_2$, $CeO_2$, $SiO_2$, or combinations thereof.

19. The process of claim 18, wherein when the support material comprises $Al_2O_3$, the support material has an $Al_2O_3$ content between 25 wt % and 75 wt %, based on a total weight of the support material.

20. The process of claim 16, wherein the oligomerization catalyst further comprises a complexing agent, the complexing agent comprising methanol, ethanol, isopropanol, n-propanol, neopentyl alcohol, dimethyl ether, diethyl ether, diisopropyl ether, diisobutyl ether, di-tert-butyl ether, methyl tert-butyl ether, ethylene glycol, 2,2-dimethylbutanol, 2,2-dimethylpentanol, 2,2-dimethylhexanol, or benzyl alcohol.

* * * * *